United States Patent [19]

Litman et al.

[11] 4,391,904

[45] * Jul. 5, 1983

[54] TEST STRIP KITS IN IMMUNOASSAYS AND COMPOSITIONS THEREIN

[75] Inventors: David J. Litman, Cupertino; Edwin F. Ullman, Atherton, both of Calif.

[73] Assignee: Syva Company, Palo Alto, Calif.

[*] Notice: The portion of the term of this patent subsequent to Nov. 10, 1998, has been disclaimed.

[21] Appl. No.: 255,022

[22] Filed: Apr. 17, 1981

Related U.S. Application Data

[63] Continuation-in-part of Ser. No. 106,620, Dec. 26, 1979, Pat. No. 4,299,916.

[51] Int. Cl.³ ............... G01N 33/54; G01N 21/00; G01N 1/48; G01N 21/06

[52] U.S. Cl. ............... 435/7; 435/188; 435/805; 435/810; 436/536; 436/537; 422/55; 422/56

[58] Field of Search ............ 424/1, 8, 12; 435/7, 435/188, 174, 178, 179, 180, 181, 810, 805; 23/230 B, 832; 422/55, 56

[56] References Cited

U.S. PATENT DOCUMENTS

| | | | |
|---|---|---|---|
| 3,850,752 | 11/1974 | Schuurs et al. | 435/7 |
| 4,059,407 | 11/1977 | Hochstrasser et al. | 435/7 |
| 4,067,959 | 1/1978 | Bolz | 23/230 B |
| 4,071,315 | 1/1978 | Chateau | 435/7 |
| 4,094,647 | 6/1978 | Deutsch et al. | 435/7 |
| 4,168,146 | 9/1979 | Grubb et al. | 435/7 |
| 4,184,920 | 1/1980 | Blixt et al. | 435/805 |
| 4,208,479 | 6/1980 | Zuk et al. | 435/7 |
| 4,230,797 | 10/1980 | Boguslaski et al. | 435/810 |
| 4,233,402 | 11/1980 | Maggio et al. | 23/230 B |
| 4,299,916 | 11/1981 | Litman et al. | 435/7 |

*Primary Examiner*—Thomas G. Wiseman
*Attorney, Agent, or Firm*—Bertram I. Rowland

[57] ABSTRACT

An assay method and compositions are provided for determining the presence of an analyte in a sample. The analyte is a member of an immunological pair (mip) of immunogens—ligand and receptor. The method has two basic elements: a solid surface to which one of the members of the immunological pair is bonded and a signal producing system, which includes a catalytic member bonded to a mip, which signal producing system results in a measurable signal on said solid surface related to the amount of analyte in the medium. The signal generating compound is produced without separation of the catalyst labeled mip bound to the solid surface from the catalyst labeled mip free in solution.

In a preferred embodiment, an enzyme is bonded to a mip which acts in conjunction with a solute to produce a signal generating product which binds preferentially to the solid surface when the enzyme is bound to the surface, resulting in a signal which is readily differentiated from signal generating compound produced by the catalyst and solute in the bulk solution.

9 Claims, No Drawings

TEST STRIP KITS IN IMMUNOASSAYS AND COMPOSITIONS THEREIN

REFERENCE TO RELATED APPLICATIONS

This application is a continuation-in-part of application Ser. No. 106,620, filed Dec. 26, 1979, now U.S. Pat. No. 4,299,916.

BACKGROUND OF THE INVENTION

1. Field of the Invention

There is continuing interest in developing new, simpler and more rapid techniques to measure the presence of an analyte in a sample suspected of containing an analyte. The analyte may be any of a wide variety of materials, such as drugs, naturally occurring physiological compounds, pollutants, fine chemicals, contaminants, or the like. In many cases, speed is important for the measurement, particularly with certain physiologically active compounds. In other situations, convenience can be a major consideration.

One convenient technique which has found wide application is the use of a "dip stick." Having a solid rod or film which can be dipped in a sample and then subsequently processed to produce a signal based on the amount of analyte in the original sample can provide many conveniences. There is ample instrumentation to measure a signal, such as light absorption or fluorescence, of a compound bound to a solid surface. Also, the dip stick allows for convenient handling, transfers, separations, and the like.

In developing an assay, it is desirable that there be a minimum number of steps and transfers in performing the assay, as well as a minimum number of separate reagents. Therefore, while a dip stick adds a convenience to separations, the separations in themselves are undesirable. Furthermore, the fewer the reagents that have to be packaged, added, and formulated, the fewer the errors which will be introduced into the assay and the greater economies and convenience of the assay.

It is therefore desirable to develop new assay methods, particularly employing rigid solid surfaces which may or may not be separated from the assay medium for measurement, where the signal may be developed without concern as to the presence of reagents in the solution affecting the observed signal on the solid surface.

2. Brief Description of the Prior Art

Patents concerned with various immobilized reagents in different types of test strips include U.S. Pat. Nos. 3,993,451; 4,038,485; 4,046,514; 4,129,417; 4,133,639; and 4,160,008, and Ger. Offen. No. 2,636,244. Patents disclosing a variety of methods involving separations of bound and unbound antigen include U.S. Pat. Nos. Re. 29,169; 3,949,064; 3,984,533; 3,985,867; 4,020,151; 4,039,652; 4,067,959*; 4,108,972; 4,145,406; and 4,168,146*.

(*Patents of particular interest)

SUMMARY OF THE INVENTION

A method is provided employing a relatively rigid insoluble, preferably bibulous, surface to which is conjugated a member of an immunological pair (abbreviated as "mip") the immunological pair consisting of ligand and a receptor which specifically binds to the lignd or their functional equivalent for the purposes of this invention. In addition to the surface, a signal producing system is provided which has as one member a catalyst, normally an enzyme, which is conjugated to a mip. Depending upon the amount of analyte present, the catalyst labeled mip will be partitioned between the bulk solution of the assay medium and the surface. The signal producing system provides a signal generating compound at the surface which generates a signal which is not significantly affected by any signal generating compound produced or present in the bulk solution. Therefore, the signal generating compound may be generated in the assay medium in the presence of unbound catalyst labeled mip. When the only catalyst in the signal producing system is the catalyst-labeled-mip, various expedients can be employed to enhance the difference in the rate of formation of the signal generating compound at the surface as compared to the bulk solution, e.g. enhancing the catalyst turnover rate at the surface. In addition to enhance the simplicity of this protocol, the last of the components of the signal generating system will be added at about the time of or before the addition of the catalyst bound to the mip.

Compositions are provided for performing the assay comprising combinations of the surface and various reagents in relative amounts for optimizing the sensitivity and accuracy of the assay.

The subject assay provides for a convenient method for detecting and measuring a wide variety of analytes in a simple, efficient, reproducible manner, which can employ visual inspection or conventional equipment for measuring a spectrophotometric property of a product bound to a surface.

DESCRIPTION OF THE SPECIFIC EMBODIMENTS

In accordance with the subject invention, an assay method and compositions are provided for measuring a wide variety of analytes, where the analyte is a member of an immunological pair (mip), the pair consisting of a ligand and a receptor (antiligand) which specifically binds to the ligand, or their functional equivalent for the purposes of the assay. The assay method has two essential elements: a surface to which is conjugated a mip; and a signal producing system which results in a signal generating compound associated with the surface, producing a detectible signal in an amount related to the amount of analyte in the assay medium. Preferably, the signal producing system will effect a two or more step conversion involving one or more compounds to produce, block or destroy the signal generating compound, where the rate of change in the concentration of the signal generating compound is related to the average distance between two molecules on the surface. The molecules may be the same or different. The immunological binding at the surface allows for localized enhanced concentrations of compounds of the signal producing system at the surface. Also, one may employ a scavenger as a third component which acts to inhibit the operation at the signal producing system in the bulk solution by scavenging an intermediate, catalyst or signal generating compound in the bulk solution.

The surface may be any convenient structure which substantially retains its form and may be separable from or part of the container. The manner of binding of the mip to the surface is not a critical aspect of this invention, so long as a sufficient amount of the mip is exposed to allow for binding to its homologous partner.

The signal producing system has at least two members: A catalyst, normally an enzyme, conjugated to a mip; and a solute which undergoes a reaction with a substance bound to the surface, and thereby directly or indirectly enhances or inhibits the production of a detectible signal. The association of a member of the signal producing system with the surface may be as a result of insolubilization, complexation with a compound on the surface or interaction, including reaction, with a compound on the surface.

Where an intermediate material is produced by the signal producing system in soluble form, both in the bulk solution and at the surface, a scavenger can advantageously be employed, so as to substantially minimize the interaction of the intermediate material produced in the bulk solution with the surface.

A wide variety of different systems may be employed for altering the degree of production of the product at the surface as compared to the bulk solution and for inhibiting intermediates or product produced in or migrating into the bulk solution from interacting with the surface. Depending upon the particular protocols, various additions, incubation steps, and reagents will be employed.

By providing for the production of a detectible signal generating material on the surface that is related to the amount of analyte in a sample, one can relate the signal level detected from the surface to the amount of analyte in the solution. By employing standards having known amounts of analyte under the same or substantially the same conditions as with an unknown, one can quantitate the detected signal level with the amount of analyte in the sample.

In accordance with the subject invention, the method is performed without requiring a separation of bound and unbound catalyst-bound-mip, nor requiring a separation of analyte from the remainder of the sample, although the latter may be desirable. This provides substantial advantages in the convenience of the protocol and in avoiding the difficulties in achieving a clean separation.

The subject invention achieves a precise, specific and sensitive technique for detecting and measuring ligands and ligand receptors. The method provides for the preferential production, inhibition of production or destruction of a compound at a rigid surface, which compound is involved with the generation of a signal at the surface. The signal generating compound associated with the surface will be of a sufficient depth or on in the surface to provide a measurable signal.

For a large number of analytes, the concentration range of interest will fall between 100 μg to one pg per ml. For many analytes, the concentration range of interest will vary from about two-fold to 100-fold so that a quantitative determination will require the ability to distinguish small differences in the concentration of the analyte in the assay medium. Immunoassays are predicated on detecting the complexation between ligand and receptor, where one or both may be labeled. The lower the concentration of the analyte, the fewer the number of complexes which are formed. Therefore, in order to be able to accurately determine the number of labeled complexes which are formed, either the label must provide a signal which can be efficiently counted at an extremely low level of events, e.g. radioactive emission, or the complex must permit amplification or multiplication, e.g. fluorescence or a catalyzed reaction.

When employing an amplification system, many problems are encountered. One serious problem is signal resulting from other than labeled complexes, namely background. Background signal can result from materials in the sample; labeled contaminants when labeling the member of the immunological pair, and unbound labeled member. In developing an assay, the signal generated by labeled complexes must not be obscured by the signal from the background and must be substantially greater than the background signal. Therefore any amplification achieved by the signal generating system must be primarily, if not solely, associated with the labeled complex rather than with background label.

In many assay techniques a clean separation of labeled immune complex and background label is required, where careful attention must be given to non-specific effects. For example, where a fluorescent label is employed in a heterogeneous system, e.g. dipstick, after combining all of the reagents with the dipstick, the dipstick must be removed and carefully washed to remove any fluorescer which is non-specifically bound. Furthermore, the number of fluorescers involved with a complex is limited to the number which can be conveniently conjugated to a member of an immunological pair, although further amplification can be obtained by employing a second labeled receptor which binds to a first receptor which binds to a ligand analyte. This step requires an additional reagent, another addition and a careful separation to avoid non-specific interactions.

The subject invention obviates or minimizes many of the shortcomings of other methods. For each complex a plurality of signal generating events are achieved by employing a catalyst. The catalyst is partitioned between the bulk solution and a surface in proportion to the amount of analyte in the assay medium. The production of signal generating product resulting from the catalyzed reaction at the surface is substantially independent of concurrent production of signal generating product, if any, produced in the bulk solution. Thus, the assay operates with the catalyst present in the bulk solution during the time the modulation of the amount of signal generating compound at the surface is occurring. The need for separating the surface from the bulk solution, whether careful or not, for measuring the signal is avoided in the subject invention, although the separation may be preferable.

Furthermore, in the subject invention, the signal generating compound can be of substantial depth on or in the surface. The presence of the catalyst at the surface allows for the deposition or conversion of a large number of signal generating compounds to provide a strong signal. This is of great importance when the measurement is visual inspection, particularly where the signal generation involves the absorption of light.

Before further describing the invention, a number of terms will be defined.

DEFINITIONS

Analyte—the compound or composition to be measured, which may be a ligand, which is mono- or polyepitopic, usually antigenic or haptenic, a single or plurality of compounds which share at least one common epitopic or determinant site or a receptor.

Specific binding pair—two different molecules, where one of the molecules has an area on the surface or in a cavity which specifically binds to a particular spatial and polar organization of the other molecule. The members of the specific binding pair are referred to as ligand and receptor (antiligand). These will be referred to in the subject application as members of an immunological pair, abbreviated as "mip". Homologous or complementary mips are ligand and receptor, while analogous mips are either ligands or receptors, which are differentiated in some manner, e.g. labeling.

Ligand—any organic compound for which a receptor naturally exists or can be prepared.

Receptor (antiligand)—any compound or composition capable of recognizing a particular spatial and polar organization of a molecule i.e. epitopic or determinant site. Illustrative receptors include naturally occurring receptors, e.g. thyroxine binding globulin, antibodies, enzymes, Fab fragments, lectins, nucleic acids and the like.

Ligand Analog—a modified ligand which can compete with the analogous ligand for a receptor, the modification providing means to join a ligand analog to another molecule. The ligand analog will usually differ from the ligand by more than replacement of a hydrogen with a bond which links the ligand analog to a hub or label, but need not.

Poly(ligand-analog)—a plurality of ligands or ligand analogs covalently joined together, normally to a hub nucleus. The hub nucleus is a polyfunctional material, normally polymeric, usually having a plurality of functional groups e.g. hydroxy, amino, mercapto, ethylenic, etc. as sites for linking. The hub nucleus is normally water soluble or at least dispersible and will usually be at least about 35,000 daltons, but generally not exceeding about 600,000 daltons. Illustrative hub nuclei include polysaccharides, polypeptides, including proteins, nucleic acids, ion exchange resins and the like.

Surface—the surface will be non-dispersed and of a dimension of at least about 1 $\mu m^2$ and generally greater, often at least about 1 $mm^2$, frequently from about 0.5 $cm^2$ to 10 $cm^2$, usually being on a support when less then about 0.5 $cm^2$; and may be of any material which is insoluble in water and provides the necessary properties for binding of a mip and a detectible signal generating compound to provide a desired signal level. Desirably, the surface will be gelatinous, permeable, porous or have a rough or irregular structure, which may include channels or indentations, generally having a substantial void volume as compared to total volume. Depending upon the nature of the detectible signal generating compound, the surface will be adsorbent or non-adsorbent, preferably being weakly or non-adsorbent. The surface may be transparent or opaque, a single material or a plurality of materials, mixtures or laminates. A wide variety of materials and shapes may be employed. The surface will be capable of substantially retaining its integrity under the conditions of the assay so that substances which are bound to the surface will remain bound to the surface and not diffuse into solution.

Signal producing system—the signal producing system has at least two members: (1) a catalytic member; and (2) a solute, which undergoes a reaction catalyzed by the catalytic member, which leads directly or indirectly to a product on or in the surface which provides a detectible signal. Desirably, a third compound will be present which provides for enhanced rate of change of the signal generating compound at the surface as compared to the bulk solution. This can be as a result of the component being bound to the surface or interacting with another member of the signal producing system.

The catalytic member may be enzymatic or non-enzymatic, preferably enzymatic. Whther one or more than one enzyme is employed, there will be at least one enzyme bound to a mip. (An enzyme acting as a catalyst should be distinguished from an enzyme acting as a receptor.)

The solute can be any compound which is capable of undergoing a reaction catalyzed by a catalytic member of the signal producing system, which reaction results either directly or indirectly in modulating the formation of a detectible signal generating compound associated with the surface. The association of the signal generating compound to the surface may be as a result of insolubilization of the product produced when solute undergoes the catalyzed reaction, complexation of the product with a compound on the surface or reaction or interaction of a compound on the surface with the product of the catalyzed reaction.

The signal generating compound will provide an electromagnetic signal, e.g. a spectrophotometric or visible, electrochemical or electronic detectible signal. The signal generating compound will be associated with the surface due to its insolubility, or covalent or non-covalent binding to the surface. The observed detectible signal from the surface will be related to the amount of catalyst bound to the surface through the binding of the catalyst-bound-mips to the mip-bound-surface.

Various techniques and combinations of reagents may be employed to enhance the production of the detectible signal at the surface, while minimizing interference from materials in the bulk solution.

Label—the label may be any molecule conjugated to another molecule where each of the molecules has had or can have had a prior discrete existence. For the most part, labels will be compounds conjugated to a mip. In referring to a catalyst conjugated to an antiligand, the reagent will be referred to as a catalyst-bound-antiligand, while for a ligand conjugated to a surface, the reagent will be referred to as ligand-bound surface.

METHOD

The subject assay is carried out in an aqueous zone or medium, where the final assay medium may be the result of prior individual additions of reagents or combinations of reagents and incubations, prior separations involving removal of the surface from an aqueous medium and transfer to a different aqueous medium having one or more reagents, or combinations thereof. The subject method, however, does not require a separation of catalyst-bound-mip which is unbound from that which is bound to its homologous partner bound to the surface (mip-bound-surface). The medium consists of a liquid phase and a non-fluid phase which is the "surface."

In carrying out the assay, the mip-bound surface will be contacted by the sample, and by the members of the signal producing system, and any ancillary materials in an aqueous medium, either concurrently or stepwise, to provide a detectible signal associated with the surface. The detectible signal will be related to the amount of the catalyst-bound-mip bound to the surface, which in turn will be related to the amount of analyte in the sample. Depending upon the nature of the signal producing system and the desired method for detecting the signal, the surface may be read in the assay medium or will be read separate from the assay medium.

In carrying out the assay, an aqueous medium will normally be employed. Other polar solvents may also be included, usually oxygenated organic solvents of from 1-6, more usually from 1-4 carbon atoms, including alcohols, ethers and the like. Usually these cosolvents will be present in less than about 40 weight percent, more usually in less than about 20 weight percent.

The pH for the medium will usually be in the range of about 4-11, more usually in the range of about 5-10, and preferably in the range of about 6.5-9.5. The pH is chosen so as to maintain a significant level of specific binding by the receptor while optimizing signal producing efficiency. In some instances, a compromise will be made between these two considerations. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the assay. Constant temperatures during the period of the measurement are generally required only if the assay is performed without comparison with a control sample. The temperatures for the determination will generally range from about 10°-50° C., more usually from about 15°-45° C.

The concentration of analyte which may be assayed will generally vary from about $10^{-4}$ to $10^{-15}$ M, more usually from about $10^{-6}$ to $10^{-13}$ M. Considerations such as whether the assay is qualitative, semi-quantitative or quantitative, the particular detection technique and the concentration of the analyte of interest will normally determine the concentration of the other reagents.

The concentrations of the various reagents will vary widely depending upon which protocols are employed, the nature of the analyte, the mip which is bound to the surface and the mip which is bound to the catalyst, the required sensitivity of the assay, and the like. In some instances, large excesses of one or the other of the mips may be employed, while in some protocols the sensitivity of the assay will be responsive to variations in the mip ratios.

By way of illustration, if the analyte is a polyepitopic antigen, one could have excesses of antiligand as antiligand-bound-surface and as catalyst-bound-antiligand, without seriously affecting the sensitivity of the assay, provided that the surface is first contacted by the sample, followed by contact with the signal producing system. Where antiligand is the sample and the protocol involves the combination of the analyte and catalyst-bound-antiligand prior to contacting the antigen-bound-surface, the sensitivity of the assay will be related to the ratios of the analyte and catalyst-bound-antiligand concentration.

In addition to the considerations involving the protocol, the concentration of the reagents will depend on the binding constant of the antiligand, the binding constant profile for a particular antisera, as well as the required sensitivity of the assay. Also, when all of the signal producing system is present in the liquid phase, the catalyst substrates and ancillary reagents should be at a concentration which allows for substantial immunological pair binding before a large amount of signal producing product is formed. Where the sensitivity of the assay is concentration related, frequently the particular concentrations will be determined empirically. When the sample is combined with the homologous catalyst-bound-mip, generally the total binding site concentration of the catalyst-bound-mip will be not less than about 0.1 times the minimum concentration of interest based on binding sites of analyte and usually not more than about 1,000 times the maximum concentration of interest based on analyte binding sites, usually about 0.1 to 100 times, more usually about 0.3-10 times the maximum concentration of interest. When the analyte is preadsorbed to the mip-bound-surface, the concentration of catalyst-bound-mip will depend on the desired rate of binding to the surface, the production of interfering signal generating compound in the liquid phase, the cost of the reagent, etc.

The concentration of catalyst-bound-mip will be chosen so that the amount of catalyst-bound-mip in the void volume-liquid immediately adjacent to and occluded in the surface will not significantly interfere with the measurement of the change in concentration of the signal generating compound at the surface as a result of catalyst-bound-mip bound to the surface. The chosen concentration will be affected by the sensitivity of the measurement, the degree of quantitation desired, the accuracy with which one must distinguish the lowest concentration of interest and the like.

In most situations, the ratio of concentration in the void volume of catalyst-bound-mip unbound to the surface to catalyst-bound-mip bound to the surface should be not greater than about 100 fold, usually not greater than about 10 fold at the maximum concentration of interest of the analyte, preferably at the mid-range concentration range of interest of the analyte.

The combination of the solid surface with the sample may be prior to, concomitant with, or subsequent to combining the catalyst-bound-mip with the sample. By employing a single unit or entity as the surface, one can use the surface to concentrate the analyte in a large sample. Also, the surface allows for removal of the analyte from other materials in the sample which could interfere with the determination of the result. Therefore, a preferred embodiment will be to combine the surface with the sample, followed by removal of the surface from the sample containing medium and transfer to the assay medium.

Alternatively, one could leave the surface in contact with the sample and add the remaining reagents. It is also feasible, although in some instances not desirable, to combine the sample with the catalyst-bound-mip, followed by introduction of the surface into the assay medium. For example, with a ligand analyte, enzyme-bound-antiligand and ligand-bound-surface, this last technique could be effectively used.

Frequently, the last of the components of the signal producing system will be added at about the same time as the catalyst-bound-mip, without any intermediate step, such as separating or washing the surface.

Where a receptor is the analyte, instead of having a single immunological pair, one may employ two immunological pairs, where the receptor acts as the ligand in one pair and the receptor in the other. For example, with IgE, one could bind the allergen or antigen to the surface and bind the catalyst to anti-IgE. In this way, the IgE acts as a bridge between two mips which in themselves cannot interact. In referring to a mip, this situation should be considered a special case which is intended to be included.

In developing protocols for the method, certain basic considerations will govern the order of addition and the combinations of reagents. The first consideration is that preferably where the surface-bound-mip and the catalyst-bound-mip are different members e.g. one is ligand and one is antiligand, the two will be brought together prior to or substantially concomitant with combination with the surface. The catalyst-bound-mip and solute will preferably be combined as a single reagent, except when the solute is the substrate of the catalyst-bound-mip. Frequently, the surface and sample will be combined prior or nearly concomitant with the addition of the other reagents.

Various protocols will have various degrees of complexity. In the simpler protocols, there will be two catalysts involved in the signal producing system, one which is bound to a mip, and the other bound to the surface. One catalyst, preferably the surface-bound-catalyst, reacts with the solute to produce a first product. This first product is acted on by the second catalyst, which first product by itself or in combination with other reagents produces a second product which preferentially binds to the surface or interacts with a compound bound to the surface, when produced adjacent to the surface. This can be achieved conveniently by producing a second product which is insoluble. By insoluble is intended a solubility of less than about $10^{-3}$ M. The insoluble product may effect changes in electrical properties e.g. electrostatic or have spectrophotometric properties, including absorption in the ultraviolet or visible wavelength range, chemiluminescence, reflectance and fluorescence, preferably absorption.

In order to minimize the amount of repetition, a table is provided which assembles various illustrative protocols. While the table is directed to polyepitopic antigens, haptens can be employed in place of the antigens. However, with haptens it will normally not be convenient to bridge between receptors, and in protocols that require bridging, the addition of a poly(ligand analog) is required to provide the bridging. When the analyte is a hapten, one will normally add the hapten containing sample to the receptor. When the catalyst-bound-mip is the receptor, the mip bound to the surface is normally hapten. When the mip bound to the surface is a receptor, the mip bound to the catalyst is normally hapten. Thus, one will normally saturate a portion of the receptor binding sites with the hapten analyte and cause the remaining sites to combine with the hapten either conjugated to the surface or to the catalyst.

The antigen or polyepitopic analyte as a ligand offers additional flexibility in that the receptor may be bonded to both the catalyst and surface, without added poly(ligand analog). Where the ligand is bonded to the surface, the ligand analyte and the ligand on the surface may compete for a limited amount of labeled receptor or a polyvalent receptor act as a bridge between ligand-bound-surface and catalyst-bound-ligand. Where receptor is bound to the surface, the ligand may then act as a bridge binding simultaneously to the receptor-bound-surface and catalyst-bound-receptor, so as to bind catalyst-bound-receptor to the surface. In the latter situation, where the receptor-bound-surface and ligand containing sample are combined prior to addition of the catalyst-bound-receptor, one can have a large excess of labeled receptor since the amount of labeled receptor which binds to the surface will be directly related to the amount of ligand bound to the surface. Where receptor-bound-surface is employed with a receptor analyte, the two receptors may compete for a limited amount of catalyst-bound-antigen.

Where ligand is the analyte and ligand is bound to the surface, one will normally first combine the sample containing ligand with catalyst-bound-receptor, so that the ligand and catalyst-bound-receptor may bind and cause a reduction in the number of available sites of the receptor that can be scavenged by the ligand bound to the surface. Where receptor is bound to the surface, and ligand is the analyte, any order of mixing will be operable, although it would usually be desirable to combine the sample with the surface, before contacting the surface with the catalyst-bound-receptor. Normally, the formation of signal generating compound will be followed as a rate, observing the change in signal on the surface with time. The rate of course will be related to the amount of label which binds to the surface. This measurement may be made prior to establishing full equilibrium between the analyte, catalyst-bound-mip and mip-bound-surface, and thus the rate may vary with time.

TABLE I

Protocols

| | | Materials Added[1] | | | |
|---|---|---|---|---|---|
| Step[2] | Surface mip | Conjugated mip | Sample | Solute | Anc. Reagent |
| I    1 | ┼Ag | Ab-Cat₁ | Ag | + | + |
| II   1 |  | Ab-Cat₁ | Ag | | |
|      2 | ┼Ag | | | + | + |
| III  1 | ┼Ab | Ab-Cat₁ | Ag | + | + |
| IV   1 | ┼Ab | | Ag | | |
|      2 | | Ab-Cat₁ | | + | + |
| V    1 | Cat₂ ┼Ag | Ab-Cat₁ | Ag | + | + |
| VI   1 | | Ab-Cat₁ | Ag | + | + |
|      2 | Cat₂ ┼Ag | | | | |
| VII  1 | Cat₂ ┼Ab | Ab-Cat₁ | Ag | + | + |
| VIII 1 | Cat₂ ┼Ab | | Ag | | |
|      2 | | Ab-Cat₁ | | + | + |
| IX   1 | R ┼Ab | Ab-Cat₁ | Ag | + | + |
| X    1 | R ┼Ab | | Ag | | |
|      2 | | Ab-Cat₁ | | + | + |
| XI   1 | | Ab-Cat₁ | Ag | | |
|      2 | R ┼Ab | | | + | + |
| XIII 1 | ┼Ag | Ab-Cat₁ | Ab | + | + |
| XIV  1 | R ┼Ag | Ab-Cat₁ | Ab | + | + |
| XV   1 | Cat₂ ┼Ag | Ab-Cat₁ | Ab | + | + |

[1]Surface mip - member of an immunological pair bound to a surface in addition to other members of the signal producing system. The ┼ symbolizes the surface. Ag and Ab mean ligand and antiligand respectively, bound covalently or non-covalently to the surface, where in any given protocol the roles of Ab and Ag may be reversed.
Cat₂ - means a catalyst, usually an enzyme, which cooperates with another catalyst usually an enzyme as members of the signal producing system.
R - reagent, bound covalently or non-covalently to the surface which reacts with the product of a catalyst as part of the signal producing system.
Conjugated mip - ligand or antiligand to which a catalyst, usually an enzyme, is covalently bonded.
Cat₁ - a catalyst, usually an enzyme, which is part of the signal producing system and reacts with the solute or product formed from the solute.
Solute - a medium soluble compound which reacts with Cat₁ or Cat₂ as part of the signal producing system.
Anc. reagents - any additional reagents necessary to the signal producing system, including enzymes, enzyme substrates and cofactors, activators, scavengers and the like.
[2]Each line indicates that the materials on that line are combined prior to the addition of any of the materials on the next line. The materials on each line may be added concurrently or consecutively, although in many instances one or the other order of addition will be preferred. When the surface is combined with the sample prior to addition of the conjugated mip, the surface may or may not be separated from the sample prior to contacting the surface with the conjugated mip and other reagents. Incubation steps may be involved between steps and between the addition of materials as part of one step.

Various protocols can be involved by using one or more catalysts in combination with a solute and one or more intermediate members of the signal producing system. In developing the protocols, one is concerned with maximizing the production of the signal, so that the signal generating molecule is preferentially produced at and on the surface. Furthermore, it is desirable that the reagents be combined in as few separate formulations as possible, so as to minimize the number of measurements and additions which are required.

Where one has a catalyst bound to a mip, which reacts with the solute to produce a signal generator which precipitates within the surface pores or channels, the surface need not be separated from the assay medium for reading. If removed from the assay medium as a matter of convenience in measuring the signal generator on the surface, it need not be washed to remove any non-specifically bound signal generator or catalyst-bound-mip.

One can further enhance the localized production of the signal generator at the surface by having two or more catalysts, particularly enzymes. By employing as a solute a substrate of one of the enzymes, preferably an enzyme bound to the surface, where the product resulting from the solute is the substrate for another enzyme, normally bound to a mip, one can significantly minimize the rate of production of signal generating compound in the bulk solution produced by the enzyme bound to the mip. In effect, by having the substrate for the catalyst-bound-mip produced at the surface, one can minimize the rate of production of signal generating compound produced in the bulk solution, since the concentration of such substrate in the bulk solution will generally be quite small.

In addition to having substrate produced at the surface, other techniques may be employed to minimize production of the signal generating compound in the bulk solution. For example, in the example given above, one could employ a scavenger in the bulk solution which would act upon the product of the solute, to prevent its further reaction. Alternatively, or in addition, one can employ an enzyme inhibitor, which is added after binding of the enzyme-bound-mip to the surface which is effective with the enzyme in the bulk solution, but not effective with enzyme bound to the surface. A further alternative, is to have a reagent which is bound to the surface, which reacts with the enzyme product to produce the signal generating compound.

Another protocol involves the use of an enzyme-bound-mip which prevents the formation of the signal producing substance on the surface. For example, an enzyme may be bound to the surface which catalyzes the conversion of the solute to an intermediate product. A second enzyme bound to the surface is employed to convert this intermediate product to the signal generating compound. The enzyme-bound-mip employs another enzyme that can react with the intermediate product without forming the signal generating compound. When the enzyme-bound-mip becomes bound to the surface it inhibits the formation of the signal generating compound on the surface. This protocol provides the advantage that a minimum signal is produced when the catalyst-bound-mip is maximally bound to the surface. Thus for certain protocols in which the analyte and the catalyst-bound-mip compete for mip-bound-surface binding sites, the absence of analyte gives a minimum signal and the presence of analyte gives an increased signal.

In accordance with the above protocols, a signal generating compound is produced or destroyed at the surface in relation to the amount of analyte in a sample. The signal generating compound which is bound to the surface will be substantially unrelated to the amount of signal generating compound, if any, produced in the bulk solution. That is, to the extent that a signal generating compound is produced in the bulk solution, the amount which may diffuse from the bulk solution to the surface and be bound to the surface will be negligibly small compared to the amount of signal generating compound produced at the solid surface at the minimum signal level for the concentration range of interest of the analyte.

The choice in binding the ligand or receptor to the surface will depend on a number of factors. When a polyepitopic ligand is the analyte, the use of catalyst-bound-receptor enhances the assay response by permitting many catalysts to become bound to each molecule of the analyte that binds to the surface. The purity of the ligand or receptor will also be of significance. Since antisera are frequently heterogeneous and may have only a small proportion of the desired receptor, the use of catalyst-bound-receptor may produce excessive amounts of signal generating compound in the bulk solution. One should therefore compare the purity of the ligand to the receptor in determining to which mip the catalyst should be conjugated. Furthermore, since in many situations the concentration of the analyte of interest will be extremely low, the binding of the members of the mip may be relatively slow. Therefore, if one can use a large excess of the mip on the surface homologous to the analyte, the rate of binding of the analyte and the resultant development of the signal generating compound at the surface can be greatly enhanced.

Another consideration is the convenience and efficiency of combining the maximum number of reagents in the fewest number of formulations. By employing a system with two or more catalysts, one can combine an enzyme catalyst with the substrate of another enzyme, referred to as the solute. In addition, one can also combine any ancillary reagents necessary for the two catalysts in a single reagent, since the catalytic reaction of the enzyme cannot occur until the other enzyme produces its substrate.

As is evident, the orders of addition and combination of the various reagents, including the introduction of the surface into the assay medium can be varied widely. Where there is a competition for a limited number of binding sites, either of the ligand or the receptor, normally the sample will be initially bound to its homologous mip (counterpart) prior to the addition of a competitive analogous mip. Or, all of the reagents may be combined simultaneously. The other reagents necessary for producing the signal generating compound may then be added concurrently with the analogous mip or subsequent to combining the analogous mip. In addition, it will be desirable, particularly where the signal producing system employs a single catalyst, that the rate of formation of the signal generating compound in the assay medium be affected by a component which differentiates between the surface and the bulk solution. Factors such as the control of local change, pH, solute concentrations, etc. on the surface can be employed to produce differential enzyme activity.

Frequently, when one is combining the sample with its homologous mip bound to the surface, an incubation step will be involved, to allow for a substantial amount of the analyte to bind. A second incubation step may be involved where the catalyst-bound-analogous mip combines with the remaining binding sites of the homologous mip-bound-surface or where the ligand acts as a bridge for two receptors, one conjugated to the surface and the other conjugated to the catalyst label. Whether a second incubation step is involved will depend to a substantial degree on the rate of binding, the sensitivity required for the assay, and the rate of production of signal generating compound at the solid surface. Conveniently, one combines the catalyst-bound-mip and remaining members of the signal producing system substantially concurrently and allows the signal generating compound to be produced while the catalyst-bound-mip is binding to the surface.

The following are illustrative of a few exemplary protocols. In the first exemplary protocol, a single enzyme catalyst is employed, which is bound to a receptor e.g. antibody. A porous surface is employed to which is also bound receptor. The sample containing polyepitopic ligand analyte is combined with the antibody-bound-surface and the mixture incubated for a sufficient time, so that a detectable amount of analyte would have had an opportunity to bind. To the mixture is then added the enzyme-bound-antiligand and the mixture incubated again for a sufficient time for a detectable amount of the enzyme conjugate to bind to ligand bound to the surface. Buffer may be included with the enzyme-bound-antiligand to enhance the binding of the enzyme conjugate to the ligand.

After sufficient incubation, the solute and any other reagents for measuring enzyme activity may be introduced as a single reagent, including an agent which enhances the enzyme activity at the surface as compared to the bulk solution, for example, a macromolecular enzyme inhibitor e.g. polyantienzyme. The inhibitor would be sterically precluded from binding to enzyme bound to the surface. Alternatively, one or more or all of the necessary substrates or cofactors may be combined with the enzyme-bound-antiligand and introduced with the enzyme-bound-antiligand into the assay medium. So long as an essential component for the enzyme reaction is withheld, the other reagents necessary for the enzyme reaction may be included with the enzyme as a single reagent. After adding the necessary reagents for the enzyme reaction, one can wait a sufficient time period for the signal generating compound to be produced within the porous surface and compare the signal thus produced to a reference signal, e.g. signal produced with a known amount of analyte. Alternatively, one could take two readings and determine the change in intensity of the signal with time. Another possibility is after a predetermined time from the complete addition of all of the substrates and cofactors necessary for the enzyme, the surface is removed and read outside of the assay medium.

As distinct from using the ligand as a bridge, a hapten analyte is illustrative of a competition mode. In this exemplary protocol, the sample containing the hapten analyte would be combined with enzyme-bound-receptor and the hapten-bound-surface to which is bonded a precursor to the signal generating compound and, as appropriate, the mixture incubated for a sufficient time for the hapten to bind to the receptor and the enzyme-bound-receptor to the surface. The solute and ancillary reagents are then added to the assay medium where the enzyme produces a product which reacts with the precursor to produce the signal generating compound. One could then take one or more readings at predetermined time intervals to determine the rate at which the signal generating compound is produced on the solid surface, which would be related to the number of available binding sites of the receptor after binding of the hapten analyte in the sample.

Another alternative with a single enzyme is to employ an oligomeric substrate with an exohydrolase. For example, one could have a disaccharide bonded to a dye which provides a colorless reagent, which on removal of the sugar provides an insoluble colored dye. Since the disaccharide requires two enzymatically catalyzed hydrolyses, in effect one has a third component since the one enzyme acts on two different substrates. There is, therefore, an analogous situation to the two enzyme system, where the action of one enzyme in a first stage produces as a product a substrate for a second enzyme, which acts in a second stage. With such a substrate, the inclusion of an agent that enhances the enzyme activity at the surface as compared to the bulk solution is of less importance.

In a third exemplary protocol, employing two enzymatic catalysts, both an enzyme and antibody would be bound to the surface (enzyme and antibody-bound-surface). The surface would be combined with a polyepitopic antigen analyte and the mixture incubated for a sufficient time for the antigen to bind to the receptor on the surface. Normally, the binding of the antigen will be performed in the undiluted sample. To the mixture may then be added as a single reagent the enzyme catalyst bound receptor, the solute, which is the substrate for the enzyme bound to the surface, and the remaining reagents, including any additional precursors to the signal generating compound where the product resulting from the solute is not the only precursor to the signal generating compound. Alternatively, the surface can be transferred to this single reagent. As previously indicated, the signal may be read on the surface in the assay medium, or the surface may be removed from the assay medium and read elsewhere. The signal which is detectable from the surface will be proportional to the amount of catalyst-bound-mip bound to the surface, which in turn is proportional to the amount of analyte in the sample.

Instead of having a second enzyme on the surface, one could bind two different enzymes on different mips, either both on ligands or both on receptors, or both enzymes on the same mip. The significant factor is that the immunological pair binding results in the enhanced localized concentration of two members or molecules of the signal producing system at the surface, which members interact to enhance the change in concentration of the signal generating compound, without reacting with each other.

The employment of a two stage process for modulation of the signal generating compound may or may not involve a third reagent in addition to the solute and catalyst-bound-mip as a component of the signal producing system. The significant factor is that the immunological binding at the surface provides an opportunity for concentrating components of the signal producing system at the surface as compared to the bulk solution.

Where the cooperation or interaction of the components of the signal producing system in the overall rate of production or destruction of the signal generating compound is related to the average spatial proximity of the components of the signal producing system, the binding of the catalyst-bound-mip through immunological pair binding to the surface permits enhancement of the localized concentration of components of the signal producing system as compared to the bulk solution, so as to minimize the effect of any generation of signal generating compound in the bulk solution on the amount of signal generating compound at the surface.

Alternatively or in addition, a scavenger can be added which preferentially reacts or interacts with a component of the signal producing system other than the solute in the bulk solution. The scavenger acts to interfere with the operation of the signal producing system in the bulk solution by either preventing a catalyzed or non-catalyzed reaction from proceeding or preventing a signal generating compound from generating a signal.

Normally, the signal will be by observation of electromagnetic radiation, particularly ultraviolet or visible light, either absorption or emission, particularly absorption, or electrical properties of the surface. Desirably, light will be in the range from about 250 to 800 nm, usually from about 350 to 700 nm. Visual inspection, reflectometers, fluorometers, spectrophotometers or the like may be employed, depending upon the signal generating compound and the nature of the surface, that is, whether opaque or transparent. Usually, it will be the intensity (transmission or emission) of the signal generator on the surface which will be correlated with the amount of analyte.

The temperature at which the signal is observed will generally range from about $-190°$ to $50°$ C., more usually from about $15°$ to $40°$ C.

Standard samples can be prepared which have known amounts of analyte. The observed signal for each of the standard samples may then be plotted or compared visually, so as to relate concentration to signal. Alternatively, a number of surfaces may be prepared relating to various concentrations, and visual or spectroscopic comparison made between the surface of the sample and the standards. Depending upon the accuracy required, the standards may be made as a prior color chart or may be made by the analyst determining the sample. Once a standard curve has been established, an observed signal may be directly related to the concentration of the analyte.

In a preferred method for calibration, a surface is employed that is identical to the surface employed in the assay but without a mip bound to it. For the assay of a polyepitopic antigen using receptor-bound-surface and catalyst-bound-receptor, the failure of catalyst-bound-receptor to bind to the surface indicates that no antigen is present in the sample. Since the calibration surface cannot bind catalyst-bound-receptor even in the presence of antigen, the surface provides a suitable comparison for negative samples when subjected to the identical protocol as the mip-bound surface employed with the sample. By comparing the signal from the calibration surface with the signal from the mip-bound-surface, any difference is indicative of the presence of antigen.

Another alternative is to employ a calibration system involving mips different from the analyte and its homologous mip. Conveniently, one would modify the catalyst or catalyst-bound-mip with a hapten recognized by a receptor bound to the calibration surface or employ a receptor for a natural site on the catalyst or catalyst-bound-mip unrelated to the specific mip binding.

By adjustment of the concentration of the receptor on the calibration surface a simulated assay response can be produced that is identical to the signal produced by a predetermined (usually zero) concentration of analyte.

As stated above, the calibration surface and the assay surface (mip-bound-surface) are subjected to identical assay conditions and the signals compared. Depending upon whether an increase or decrease in signal results from an elevation in analyte concentration, a difference in signal between the calibration surface and the assay surface in the appopriate direction would indicate the presence of analyte.

The time for measuring the signal will be based on such factors as the sensitivity required, concentration of analyte, rate of binding, nature of the signal producing system, etc. Since at zero time there is no change in the initial signal, a single measurement need only be made at the end of the final incubation. For better quantitation, measurements could be made at intervals during the incubation, with incubation time varying from 5 secs to 36 hrs.

The ligand analyte may be mono- or polyepitopic. Except that a hapten cannot be employed as a bridge between the receptor bound to the surface and catalyst-bound-receptor, hapten and antigen analytes can be treated analogously. If a bridge is desired, a poly(ligand analog) may be employed having a plurality of haptens joined together and employing a limited amount of catalyst-bound-receptor. In this protocol, the receptor-bound-surface would be combined with the sample and poly(ligand analog), followed by addition of catalyst-bound-receptor. Of course, one could replace the poly(ligand analog) and catalyst-bound-receptor, by hapten conjugated to the catalyst (hapten-bound-catalyst).

Where the receptor is the analyte, one can allow for competition between the receptor analyte and receptor-bound-surface for a limited amount of catalyst-bound-ligand. For a receptor analyte, alternatively, one could employ the antigen as a bridge as described previously, where the receptor analyte competes with catalyst-bound-receptor for the antigen bound to the receptor as receptor-bound-surface.

In the event that the analyte, the mip-bound-surface, and the catalyst-bound-mip are all the same member, then the homologous member must be added and in polyepitopic form either, for example, for receptor, as an antibody or a polyvalent receptor, where the receptor is other than an antibody, or for ligand, as poly-hapten (poly(ligand analog)) or polyepitopic antigen.

The subject method lends itself to the determination of a plurality, two or more, analytes simultaneously. By having a surface e.g. a strip, with a plurality of mips for different analytes, e.g. antigens, so that each mip is localized at a particular position on the solid surface, in combination with a plurality of catalyst-bound-mips, specific for each analyte, generation of signal at each site would be indicative of different analytes.

MATERIALS

The components employed in the subject assay will be the analyte; the surface; the signal producing system; and as appropriate poly(ligand analog) or polyvalent receptor. The signal producing system will have at least two members, the catalyst-bound-mip and the solute, frequently having additional members.

ANALYTE

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof. Such combinations of assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight;

among the hormones of interest, the molecular weights will usually range from about 5,000 to 60,000 molecular weight.

The wide variety of proteins may be considered as to the family of proteins having similar structural features, proteins having particular biological functions, proteins relates to specific microorganisms, particularly disease causing microorganisms, etc. For cells and viruses, histocompatability antigens or surface antigens will frequently be of interest.

The following are classes of proteins related by structure:
protamines
histones
albumins
globulins
scleroproteins
phosphoproteins
mucoproteins
chromoproteins
lipoproteins
nucleoproteins
glycoproteins
proteoglycans
unclassified proteins, e.g. somatotropin, prolactin, insulin, pepsin A number of proteins found in the human plasma are important clinically and include:
Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor $\alpha_1$-glycoprotein
$\alpha_1$X-Glycoprotein
Thyroxin-binding globulin
Inter-$\alpha$-trypsin-inhibitor
Gc-globulin
  (Gc 1-1)
  (Gc 2-1)
  (Gc 2-2)
Haptoglobin
  (Hp 1-1)
  (Hp 2-1)
  (Hp 2-2)
Ceruloplasmin
Cholinesterase
$\alpha_2$-Lipoprotein(s)
Myoglobin
C-Reactive Protein
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G (IgG) or $\gamma$G-globulin
Mol. formula: $\gamma_2\kappa_2$ or $\gamma_2\lambda_2$
Immunoglobulin A (IgA) or $\gamma$A-globulin
Mol. formula: $(\alpha_2\kappa_2)^n$ or $(\alpha_2\lambda_2)^n$
Immunoglobulin M (IgM) or $\gamma$M-globulin
Mol. formula: $(\mu_2\kappa_2)^5$ or $(\mu_2\lambda_2)^5$
Immunoglobulin D(IgD) or $\gamma$D-globulin ($\gamma$D)
Mol. formula: $(\delta_2\kappa_2)$ or $\delta_2\lambda_2$
Immunoglobulin E (IgE) or $\gamma$E-Globulin ($\gamma$E)
Mol. formula: $(\epsilon_2\kappa_2)$ or $(\epsilon_2\lambda_2)$
Free $\kappa$ and $\lambda$ light chains
Complement factors:
C'1
  C'1q
  C'1r
  C'1s
C'2
C'3
  $\beta_1$A
  $\alpha_2$D
C'4
C'5
C'6
C'7
C'8
C'9

Important blood clotting factors include:

| BLOOD CLOTTING FACTORS | |
|---|---|
| International designation | Name |
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:

Peptide and Protein Hormones

Parathyroid hormone (parathromone)
Thyrocalcitonin
Insulin
Glucagon
Relaxin
Erythropoietin
Melanotropin (melanocyte-stimulating hormone; intermedin)
Somatotropin (growth hormone)
Corticotropin (adrenocorticotropic hormone)
Thyrotropin
Follicle-stimulating hormone
Luteinizing hormone (interstitial cell-stimulating hormone)
Luteomammotropic hormone (luteotropin, prolactin)
Gonadotropin (chorionic gonadotropin)

Tissue Hormones

Secretin
Gastrin

Angiotensin I and II
Bradykinin
Human placental lactogen

Peptide Hormones from the Neurohypophysis

Oxytocin
Vasopressin
Releasing factors (RF) CRF, LRF, TRF, Somatotropin-RF, GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
|---|---|
| *Streptococcus pyogenes* | Polysaccharide |
| *Diplococcus pneumoniae* | Polysaccharide |
| *Neisseria meningitidis* | Polysaccharide |
| *Neisseria gonorrheae* | Polysaccharide |
| *Corynebacterium diphtheriae* | Polysaccharide |
| *Actinobacillus mallei;* | Crude extract |
| *Actinobacillus whitemori* | |
| *Francisella tularensis* | Lipopolysaccharide |
| | Polysaccharide |
| *Pasteurella pestis* | |
| *Pasteurella pestis* | Polysaccharide |
| *Pasteurella multocida* | Capsular antigen |
| *Brucella abortus* | Crude extract |
| *Haemophilus influenzae* | Polysaccharide |
| *Haemophilus pertussis* | Crude |
| *Treponema reiteri* | Polysaccharide |
| *Veillonella* | Lipopolysaccharide |
| *Erysipelothrix* | Polysaccharide |
| *Listeria monocytogenes* | Polysaccharide |
| *Chromobacterium* | Lipopolysaccharide |
| *Mycobacterium tuberculosis* | Saline extract of 90% phenol extracted mycobacteria and polysaccharide fraction of cells and turberculin |
| *Klebsiella aerogenes* | Polysaccharide |
| *Klebsiella cloacae* | Polysaccharide |
| *Salmonella typhosa* | Lipopolysaccharide, Polysaccharide |
| *Salmonella typhi-murium;* | Polysaccharide |
| *Salmonella derby* | |
| *Salmonella pullorum* | |
| *Shigella dysenteriae* | Polysaccharide |
| *Shigella flexneri* | |
| *Shigella sonnei* | Crude, Polysaccharide |
| *Rickettsiae* | Crude extract |
| *Candida albicans* | Polysaccharide |
| *Entamoeba histolytica* | Crude extract |

The microorganisms which are assayed may be intact, lysed, ground or otherwise fragmented, and the resulting composition or portion, e.g. by extraction, assayed. Microorganisms of interest include:

Corynebacteria
*Corynebacterium diptheriae*
Pneumococci
*Diplococcus pneumoniae*
Streptococci
*Streptococcus pyogenes*
*Streptococcus salivarus*
Staphylococci
*Staphylococcus aureus*
*Staphylococcus albus*
Neisseriae
*Neisseria meningitidis*
*Neisseria gonorrheae*
Enterobacteriaciae

| *Escherichia coli* | } The coliform |
| *Aerobacter aerogenes* | bacteria |

| *Klebsiella pneumoniae* | |
| *Salmonella typhosa* | } The Salmonellae |
| *Salmonella choleraesuis* | |
| *Salmonella typhimurium* | |
| *Shigella dysenteriae* | |
| *Shigella schmitzii* | |
| *Shigella arabinotarda* | } The Shigellae |
| *Shigella flexneri* | |
| *Shigella boydii* | |
| *Shigella Sonnei* | |
| Other enteric bacilli | |
| *Proteus vulgaris* | |
| *Proteus mirabilis* | } Proteus species |
| *Proteus morgani* | |
| *Pseudomonas aeruginosa* | |
| *Alcaligenes faecalis* | |
| *Vibro cholerae* | |

Hemophilus-Bordetella group
*Hemophilus influenzae,*    *H. ducreyi*
                                      *H. hemophilus*
                                      *H. aegypticus*
                                      *H. parainfluenzae*
*Bordetella pertussis*
Pasteurellae
*Pasteurella pestis*
*Pasteurella tulareusis*
Brucellae
*Brucella melitensis*
*Brucella abortus*
*Brucella suis*
Aerobic Spore-forming Bacilli
*Bacillus anthracis*
*Bacillus subtilis*
*Bacillus megaterium*
*Bacillus cereus*
Anaerobic Spore-forming Bacilli
*Clostridium botulinum*
*Clostridium tetani*
*Clostridium perfringens*
*Clostridium novyi*
*Clostridium septicum*
*Clostridium histolyticum*
*Clostridium tertium*
*Clostridium bifermentans*
*Clostridium sporogenes*
Mycobacteria
*Mycobacterium tuberculosis hominis*
*Mycobacterium bovis*
*Mycobacterium avium*
*Mycobacterium leprae*
*Mycobacterium paratuberculosis*
Actinomycetes (fungus-like bacteria)
*Actinomyces israelii*
*Actinomyces bovis*
*Actinomyces naeslundii*
*Nocardia asteroides*
*Nocardia brasiliensis*
The Spirochetes
*Treponema pallidum*     *Spirillum minus*
*Treponema pertenue*     *Streptobacillus*
                                   *moniliformis*
*Treponema carateum*
*Borrelia recurrentis*
*Leptospira icterohemorrhagiae*
*Leptospira canicola*
Mycoplasmas
*Mycoplasma pneumoniae*
Other pathogens
*Listeria monocytogenes*
*Erysipelothrix rhusiopathiae*
*Streptobacillus moniliformis*
*Donvania granulomatis*
*Bartonella bacilliformis*
Rickettsiae (bacteria-like parasites)
*Rickettsia prowazekii*
*Rickettsia mooseri*
*Rickettsia rickettsii*
*Rickettsia conori*
*Rickettsia australis*

*Rickettsia sibiricus*
*Rickettsia akari*
*Rickettsia tsutsugamushi*
*Rickettsia burnetii*
*Rickettsia quintana*
Chlamydia (unclassifiable parasites bacterial/viral)

Chlamydia agents (naming uncertain)
Fungi
*Cryptococcus neoformans*
*Blastomyces dermatidis*
*Histoplasma capsulatum*
*Coccidioides immitis*
*Paracoccidioides brasiliensis*
*Candida albicans*
*Aspergillus fumigatus*
*Mucor corymbifer (Absidia corymbifera)*
*Rhizopus oryzae*
*Rhizopus arrhizus*       } Phycomycetes
*Rhizopus nigricans*
*Sporotrichum schenkii*
*Fonsecaea pedrosoi*
*Fonsecaea compacta*
*Fonsecaea dermatidis*
*Cladosporium carrionii*
*Phialophora verrucosa*
*Aspergillus nidulans*
*Madurella mycetomi*
*Madurella grisea*
*Allescheria boydii*
*Phialosphora jeanselmei*
*Microsporum gypseum*
*Trichophyton mentagrophytes*
*Keratinomyces ajelloi*
*Microsporum canis*
*Trichophyton rubrum*
*Microsporum andouini*
Viruses
Adenoviruses
Herpes Viruses
Herpes simplex
Varicella (Chicken pox)
Herpes Zoster (Shingles)
Virus B
Cytomegalovirus
Pox Viruses
Variola (smallpox)
Vaccinia
*Poxvirus bovis*
Paravaccinia
*Molluscum contagiosum*
Picornaviruses
Poliovirus
Coxsackievirus
Echoviruses
Rhinoviruses
Myxoviruses
Influenza (A, B, and C)
Parainfluenza (1-4)
Mumps Virus
Newcastle Disease Virus
Measles Virus
Rinderpest Virus
Canine Distemper Virus
Respiratory Syncytial Virus
Rubella Virus
Arboviruses
Eastern Equine Eucephalitis Virus
Western Equine Eucephalitis Virus
Sindbis Virus
Chikugunya Virus
Semliki Forest Virus
Mayora Virus
St. Louis Encephalitis Virus
California Encephalitis Virus
Colorado Tick Fever Virus
Yellow Fever Virus
Dengue Virus
Reoviruses
Reovirus Types 1-3

Hepatitis
Hepatitis A Virus
Hepatitis B Virus
Tumor Viruses
Rauscher Leukemia Virus
Gross Virus
Maloney Leukemia Virus
Epstein Barr Virus
Other Parasites Related to the Following Diseases
Dog Heart Worm (microfilaria)
Malaria
Schistosomiasis
Coccidosis
Trichinosis The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids, isoquinoline alkaloids; quinoline alkaloids; which includes quinine and quinidine; diterpene alkaloids; their derivatives and metabolites.

The next group of drugs includes steroids, which includes the estrogens, gestogens, androgens, andrenocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, ctecholamines, which includes ephedrine, L-dopa, epinephrine, narceine, papaverine, their metabolites.

The next group of drugs is aminoalkylbenzenes, with alkyl of from 2 to 3 carbon atoms, which includes ephedrine, L-dopa, epinephrine, narceine, papaverine, their metabolites and derivatives.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

The next group of compounds is amino acids and small peptides which include polyiodothyronines e.g. thyroxine, and triiodothyronine, oxytocin, ACTH, angiotensin, met- and leu-enkephalin their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Many drugs of interest will involve aralkylamine structures, which may or may not be a part of a heterocyclic structure, e.g. alkaloids, phenobarbitol, dilantin, epinephrine, L-dopa, etc. While there is some similarity in structure, the compounds vary widely as to activity.

Drugs may also be considered as to the primary purpose for which they are used. In many situations, it is desirable to monitor a drug for police functions, therapeutic dosage monitoring for drugs used for treatment of asthmatics, epileptics, cardiovascular diseases, hypertension, bacterial or viral infection, gastraintestinal infections, etc. In each case, physiological fluids such as blood, serum, saliva, etc. are monitored to ensure that the administered drug is within the therapeutic dosage for the individual.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins, IgA, IgG, IgE and IgM, the molecular weights will generally vary from about 160,000 to about $10^6$. Enzymes will normally range from about 10,000 to 6000,000 in molecular weight. Natural receptors vary widely, generally being at least about 25,000 molecular weight and may be $10^6$ or higher molecular weight, including such materials as avidin, thyroxine binding globulin, thyroxine binding prealbumin, transcortin, etc.

LIGAND ANALOG

The ligand analog will differ from the ligand either by replacement of a hydrogen or a functionality with a bond or a linking group which has a functionality for forming a covalent bond to another molecule having an active functionality, such as an hydroxyl, amino, aryl, thio, olefin, etc., where the resulting compound differs from the ligand by more than substitution of a hydrogen by the molecule to which it is conjugated. The linking group will normally have from 1-20 atoms other than hydrogen, which are carbon, oxygen, sulfur, nitrogen, and halogen of atomic number 17-35. The functionalities which are involved include carbonyl, both oxo and non-oxo, active halogen, diazo, mercapto, ethylene, particularly activated ethylene, amino, and the like. The number of heteroatoms will generally range from about 0-6, more usually from about 1-6, and preferably from about 1-4. A description of linking groups may be found in U.S. Pat. No. 3,817,837, which disclosure is incorporated herein by reference.

For the most part, the linking groups will be aliphatic, although with diazo groups, aromatic groups are involved. Generally, the linking group is a divalent chain having about 1-10, more usually from about 1-6 atoms in the chain. Oxygen will normally be present as oxo or oxy, bonded to carbon and hydrogen, preferably bonded solely to carbon, while nitrogen will normally be present as amino, bonded solely to carbon, or amido, while sulfur would be analogous to oxygen.

Common functionalities in forming the covalent bond between the linking group and the molecule to be conjugated are alkylamine, amide, amidine, thioamide, urea, thiourea, guanidine, and diazo.

Linking groups which find particular application with conjugation to polypeptides are those involving carboxylic acids which may be used in conjunction with diimides, or as mixed anhydrides with carbonate monesters or as active carboxylic esters e.g. N-hydroxy succinimide or p-nitrophenyl. Nitrogen analogs may be employed as imidoesters. Aldehydes can be used to form imines under reductive amination conditions e.g. in the presence of borohydrides, to produce alkylamines. Other non-oxo carbonyl groups which may be employed include isocyanates and isothiocyanates. In addition, active halide may be employed, particularly bromoacetyl groups.

In most instances, the ligand will have one or more functional groups which may be employed as the site for linking the linking group. Particularly, hydroxy, amino and aryl groups, particularly activated aryl groups find use. Also, oximes may be prepared from oxo functionalities and the hydroxyl used as a site for joining to a linking group, such as carboxymethyl.

The choice of linking group will vary widely, depending upon the functionalities which are present in the ligand, in the compound to which the ligand is to be conjugated, the nature and length of the linking group desired, and the like.

SOLID SURFACE

The surface can be widely varied. Usually, the surface will be chosen so as not to be strongly adsorbent for members of the signal producing system, which would deleteriously affect the assay, so as not to interfere with the measurement of the signal generated by the signal generating system and to substantially retains its physical integrity during the assay. The surface may take different forms, have different physical characteristics, can be of different chemical compositions and may be of one or more compositions as a mixture of compositions or laminates or combinations thereof. The particular surface will interact with the signal generating compound by desolubilization of the signal generating compound onto the surface, or permit complexation, reaction or interaction of a compound bonded to the surface, so as to form or destroy the signal generating compound.

The surface may be of a variety of shapes and forms, as well as of varied dimensions depending on the manner of use and measurement. The surface may be supported by a rod, tube or capillary, fiber, strip, disk, plate, cuvette, or the like. The surface will be an integral part of the support or distinct from the support as an applied layer having a relatively small thickness, usually at least 0.1μ, more usually 1μ, generally 10μ, or greater depending on the nature of the surface, ease of application and desired properties.

The surface may be opaque, translucent or transparent. It may be a solid, gel or viscous liquid, permeable or non-permeable, porous or non-porous, bibulous, reticulated, convoluted, channeled, being uneven or smooth, or coated with a continuous or discontinuous layer. Preferably, the surface will be penetrable by the signal generating compound to at least a depth of 0.1μ, more preferably at least 1μ and particularly preferred at least 10μ.

The surface may also be considered in accordance with its function. The surface serves as a base or substrate which will retain a discrete existence in the aqueous assay solution, so as to be discernable from the medium and usually separable from the medium. The surface serves to support mips which are bound to it, so that they are incapable of diffusing through the solution independent of the surface. In addition, the surface acts as a support for the signal generating compound, either as a base for a deposited layer or as a support for covalent or non-covalent attachment. The surface is effectively non-fluid, discrete in that the surface is distinguishable from the liquid medium in which the surface is immersed, and provides a distinct base or foundation for supporting mips, members of the signal generating system or other compounds as appropriate, which are bound either covalently or non-covalently. The surface may exist in a charged or non-charged form, being charged where such charge provides some advantage to the operation of the signal producing system.

Various materials may be employed, the primary considerations being the binding of the signal generating compound to the surface, the absence of interference of signal generation, the ease of conjugating to the surface, and the like.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), silicones, polyformaldehyde, cellulose, cellulose acetate, nitrocellulose, etc. Other materials which may be employed, include paper, glasses, ceramics, metals, metalloids, semiconductive materials, cermets or the like. In addition are included substances that form gels, such as proteins e.g. gelatins, lipopolysaccharides, silicates, agarose, and polyacrylamides or polymers which form several aqueous phases, such as dextrans, polyalkylene glycols (alkylene of 2 to 3 carbon atoms) or surfactants e.g. amphiphilic compounds, such as phospholipids, long chain (12-24 carbon atoms) alkyl ammonium salts and the like.

Where the solid surface is porous, various pore sizes may be employed depending upon the nature of the system. In some instances, the pore size may be limited, in order to avoid access to catalyst bound to the surface. Cut-off sizes can vary from tens of thousands, e.g. 20,000 to millions dalton, e.g. 20 million, usually cut-off size will not be less than 5000 daltons.

The particular material employed for the solid surface will be insoluble in the assay medium, may be swellable or nonswellable, preferably nonswellable, may be hydrophobic or hydrophilic, i.e. polar or non-polar, preferably hydrophilic, may be coated with a thin mono- or polymolecular layer of a different composition or uncoated, may be a single material or a plurality of materials, particularly as laminates or fibers, may be woven, cast, extruded, etched, aggregated, etc.

In preparing the surface, a plurality of different materials may be employed, particularly as laminates, to obtain various properties. For example, a porous layer may be deposited onto a nonporous transparent cuvette wall, which may provide a window for viewing the signal, while protecting the adjacent layer. A surface may be modified so as to enhance the binding characteristics of the signal generating compound, inhibit migration in a particular direction, act as a semi-permeable membrane, or the like. Protein coatings, e.g. gelatin can be employed to avoid non-specific binding, simplify covalent conjugation, enhance signal detection or the like. However, it should be appreciated that the material employed should preferably not be strongly adsorbent, so as to adsorb a signal generating compound which is produced in the bulk solution and diffuses to the surface.

The particular dimensions of the surface support will be a matter of convenience, depending upon the size of the samples involved, the protocol, the means for measuring the signal, and the like.

The surface will usually be polyfunctional or be capable of being polyfunctionalized, so as to allow for covalent bonding between the mip and the surface, as well as the other compounds which must be conjugated. Functional groups which may be present on the surface and used for linking can include carboxylic acids, aldehydes, amino groups, cyano groups, ethylenic groups, hydroxyl groups, mercapto groups and the like. The manner of linking a wide variety of compounds to the various surfaces is well known and is amply illustrated in the literature. See for example Immobilized Enzymes, Ichiro Chibata, Halsted Press, New York, 1978, and Cuatrecasas, J. Biol. Chem. 245 3059 (1970).

The length of the linking group may vary widely depending upon the nature of the compound being linked, the effect of the distance between the linked compound and the surface on the linked compound's properties, the potential for cross-linking of the linked compound, and the like.

The linking group may be a bond or have up to about 12, usually not more than about 10 atoms in a chain. The linking group may be aliphatic, alicyclic, aromatic, heterocyclic, or combinations thereof. The total number of atoms of the linking group will be not more than about 20, usually not more than about 16 atoms other than hydrogen, which will be carbon, oxygen as oxy or oxo, both oxo-carbonyl and non-oxo-carbonyl; nitrogen as amino or amido, and sulfur as thio or thiono. Illustrative groups include methylenecarbonyl, succinimidyl, α-haloacetyl, thiomethylene, glycyl or polyglycyl, succindioyl, maledioyl, glutardialkylidene, methylenephenyldiazo, and ureido.

A mip will always be bound, covalently or non-covalently to the solid surface. Depending upon the nature of the protocol, the amount of bound mip may be limited or in excess of the highest amount of analyte which can be expected to be found in the sample based on binding sites of the analyte. In addition, one or more members of the signal producing system may also be bound to the solid surface. Frequently, the amount of the member of the signal producing system which is conjugated will be rate limiting, so that large excesses will be employed.

SIGNAL PRODUCING SYSTEM

The signal producing system has at least two members: A catalyst, normally an enzyme; and a solute, which is capable of undergoing a catalyzed reaction which may directly provide the signal generating compound, may provide a precursor to the signal generating compound, or may produce a product which serves to react or interact with another compound to produce, block or destroy the signal generating compound.

Al already indicated, one or a plurality of catalysts may be employed, but usually at least one of the catalysts will be an enzyme. While there may be two or more catalysts, usually as the number of catalysts increases over three, the advantages are quickly offset by the disadvantages. Therefore, normally there will not be more than three catalysts, usually not more than two catalysts.

At least one catalyst will be bound to a mip, either covalently or non-covalently, for example through a specific binding pair. One or a plurality of the same or different catalyst molecules may be bonded to one or more mips or alternatively, a plurality of mips may be bonded to a single catalyst molecule. Where there are a plurality of catalysts, the choice of which catalyst to bond to the solid surface and/or the mip, will depend upon the conveniences involved in formulating the reagents, ease of conjugation and the effect on the sensitivity of the assay. Therefore, there frequently will be a preference as to which catalysts are conjugated to the solid surface and which catalysts are conjugated to the mip.

To provide a signal preferentially associated with the surface as compared to the bulk solution, various techniques may be used. These techniques include: insolubilization of a signal generating compound; preferential production of a signal generating compound at the surface with binding to the surface; scavenging or inhibition of catalyst-bound-mip in the bulk solution; scavenging of a catalyst, signal generating compound or a precursor in the bulk solution with the component of the signal producing system protected from the scavenger at the surface; and producing a compound at the surface which interacts, including reacts, with a compound on the surface. Not only can these various techniques be used individually, but they can also be combined with advantage.

In desolubilization to provide an insoluble signal generating compound, a compound is catalytically transformed from a soluble form to an insoluble form; for a dye from a leuco form to a colored form; for a fluorescer, from a non-fluorescent compound to a fluorescent compound.

A large number of dyes exist which are predicated on being modified to a colored form as they bind to a variety of natural fabrics. The same type of modification can be involved in the subject invention, where the dye can be desolubilized catalytically, particularly enzymatically. The desolubilization may involve oxidation, reduction, or hydrolysis, particularly of water solubilizing groups, such as organic and inorganic esters, e.g. phosphates, pyrophosphates, carboxylates, e.g. uronates, sulfates, and the like, or ethers, such as glycosidyl ethers.

A wide variety of compounds can be modified so as to enhance their hydrophobicity—lack of solubility in a aqueous medium. The compounds can then be further modified to enhance their hydrophilicity e.g. substitution with water solubilizing substituents which upon catalytic removal results in a product which has gained signal generating capability. For example, phenolic compounds can be esterified with organic or inorganic acids or etherified with sugars. Amines can be acylated. Heterocycles can be oxidized or reduced to enhance solubility or insolubility. In each instance the reactant will be incapable of signal generation, while the product will be capable of signal generation or influencing signal generation.

Various compounds may be employed as solutes which upon catalytic transformation, either in one or two steps, results in an insoluble electroactive or changed molecule, chromophore or fluorophore product as the signal generator.

In some instances a redox reaction may transform a soluble compound having light absorption at short wavelengths to an insoluble compound absorbing light at substantially longer wavelengths. When a commercially available compound which could otherwise be employed as a solute dose not provide an insoluble product, such commercially available compound could be modified in conventional ways by substitution with hydrophobic groups, such as hydrocarbon, e.g. alkyl, halo, e.g. chloro and bromo, cyano, nitro, or combinations thereof. Alternatively where the commercially available compound is insoluble, and could fulfill the requirements of a signal generating compound, such commercially available compound could be employed as a solute if substituted with a catalytically removable group which confers water solubility and which effects a substantial change in the electroactive, chromophoric or fluorophoric properties of the compound.

The subject invention also lends itself to employ colored coupling products employed in photography. By employing a catalyst other than silver, as the catalyst-bound-mip, with a substrate which can be activated to react with a compound bound to the surface to produce a colored coupling product, the signal producing system can parallel color photography. For an excellent review and list of compositions which may be employed in the subject invetion, see "The Theory of the Photographic Process," 3rd ed. Edited by T. H. James, The Macmillan Co., New York (1966) pages 383–396, which pages are incorporated herein by reference.

Of particular interest are such combinations as substituted anilines, particularly amino-substituted anilines and phenols, particularly naphthols. Individual compounds include α-benzoyl-3-[α-(4-carboxymethylphenoxy)acetamido]-acetanilide; 1-phenyl-3-[3-(4-cyanomethylphenoxy)benzamido]-5-pyrazolone; 1-[4-(3,5-dimethylphenoxy)phenyl]-3-(4-aminoethoxy-3-methylbenzamido)-5-pyrazalone; and 1-hydroxy-N-[γ-(2-tert.-amyl-4-carboxymethylphenoxy)propyl]-2-naphthamide. These compounds can be covalently conjugated to a surface or further modified with lipophilic groups to become non-covalently bound to a surface.

The following lists are compounds which may be employed as solutes, which by one or two step catalytic transformations would produce a signal generating compound. In some instances because of the solubility characteristics of the compounds, some substitution would be necessary to achieve the desired properties. The list of chromophores and fluorophores is broken down into categories of the nature of the listed reaction.

CHROMOPHORS AND FLUOROPHORE REACTIONS

Redox tetrazolium salt→formazan
leuco methylene blue→methylene blue
leuco Meldola blue→Meldola blue
4-Cl-1-naphthol→colored oxidation product
leuco phenazine methosulfate→phenazine methosulfate
N-3,5-dibromo or N-3,5-dichloro-4-hydroxyphenyl p-dimethylaminoaniline→N-(p-dimethylaminophenyl) 3,5-dibromo- or 3,5-dichloroquinone monoimine
dihydropyocyanine→pyocyanine
2-(2'-benzothiazolyl)-5-styryl-3-(4'-phthalhydrazidyl) tetrazolium chloride→formazan derivative
dihydrosafranine→safranine*
leuco benzyl viologen→benzyl viologen
diaminobenzidine→colored oxidation products
o-toluidine→colored oxidation product
α-naphthol+pyronine→fluorescent product
5-amino-2,3-dihydro-1,4-phthalazinedione→hv
aminoantipyrene+1,7-hydroxynaphthol→colored coupling product

Hydrolysis umbelliferyl phosphate→umbelliferone
2,4-dinitronaphthyl-1β-D-galactoside→2,4-dinitronaphthol N-(2'-methoxyphenyl) 6-bromo-3-carboxamide-naphthyl-2β-D-glucosiduronic acid ether→N-(2'-methoxyphenyl) 6-bromo-3-carboxamide-2-naphthol

*water soluble

The preferred spectrophotometrically active compounds—dyes, fluorescers and chemiluminescers—have hydroxyl groups, particularly one or more phenolic groups, which are present in the parent compound or may be introduced. The hydroxyl groups are convenient sites for esterification to form esters e.g. phosphates and uronates or ethers, particularly glycosidyl ethers.

As already indicated, both enzymatic and nonenzymatic catalysts may be employed. Preferably, enzymatic catalysts will be employed, since they frequently provide for more rapid reactions, a desirable versatility in the variety of reactions, and have well characterized properties.

In choosing an enzyme, there will be many considerations in addition to those involved with the reaction of interest. These considerations include the stability of the enzyme, the desirability of a high turnover rate, the sensitivity of the rate to variations in the physical environment, the nature of the substrate(s) and product(s), the availability of the enzyme, the effect of conjugation of the enzyme on the enzyme's properties, the effect on enzyme activity of materials which may be encountered in the sample solutions, the molecular weight of the enzyme, and the like.

The following are categories of enzymes as set forth in accordance with the classification of the International Union of Biochemistry.

TABLE II

| | | |
|---|---|---|
| 1. Oxiodoreductases | | |
| 1.1 | Acting on the Ch—OH group of donors | |
| | 1.1.1 | With NAD or NADP as acceptor |
| | 1.1.2 | With a cytochrome as an acceptor |
| | 1.1.3 | With O$_2$ as acceptor |
| | 1.1.99 | With other acceptors |
| 1.2 | Acting on the aldehyde or keto group as donors | |
| | 1.2.1 | With NAD or NADP as acceptor |
| | 1.2.2 | With cytochrome as an acceptor |
| | 1.2.3 | With O$_2$ as acceptor |
| | 1.2.4 | With lipoate as acceptor |
| | 1.2.99 | With other acceptors |
| 1.3 | Acting on the CH—CH group of donors | |
| | 1.3.1 | With NAD or NADP as acceptors |
| | 1.3.2 | With a cytochrome as an acceptor |
| | 1.3.3 | With O$_2$ as acceptor |
| | 1.3.99 | With other acceptors |
| 1.4 | Acting on the CH—NH$_2$ group of donors | |
| | 1.4.1 | With NAD or NADP as acceptor |
| | 1.4.3 | With O$_2$ as acceptor |
| 1.5 | Acting on the C—NH group of donors | |
| | 1.5.1 | With NAD or NADP as acceptor |
| | 1.5.3 | With O$_2$ as acceptor |
| 1.6 | Acting on reduced NAD or NADP as donor | |
| | 1.6.1 | With NAD or NADP as acceptor |
| | 1.6.2 | With a cytochrome as an acceptor |
| | 1.6.4 | With a disulfide compound as acceptor |
| | 1.6.5 | With a quinone or related compound as acceptor |
| | 1.6.6 | With a nitrogeneous group as acceptor |
| | 1.6.99 | With other acceptors |
| 1.7 | Acting on other nitrogeneous compounds as donors | |
| | 1.7.3 | With O$_2$ as acceptor |
| | 1.7.99 | With other acceptors |
| 1.8 | Acting on sulfur groups of donors | |
| | 1.8.1 | With NAD or NADP as acceptor |
| | 1.8.3 | With O$_2$ as acceptor |
| | 1.8.4 | With a disulfide compound as acceptor |
| | 1.8.5 | With a quinone or related compound as acceptor |
| | 1.8.6 | With nitrogeneous group as acceptor |
| 1.9 | Acting on heme groups of donors | |
| | 1.9.3 | With O$_2$ as acceptor |
| | 1.9.6 | With a nitrogeneous group as acceptor |
| 1.10 | Acting on diphenols and related substances as donors | |
| | 1.10.3 | With O$_2$ as acceptors |
| 1.11 | Acting on H$_2$O$_2$ as acceptor | |
| 1.12 | Acting on hydrogen as donor | |
| 1.13 | Acting on single donors with incorporation of oxygen (oxygenases) | |
| 1.14 | Acting on paired donors with incorporation of oxygen into one donor (hydroxylases) | |
| | 1.14.1 | Using reduced NAD or NADP as one donor |
| | 1.14.2 | Using ascorbate as one donor |
| | 1.14.3 | Using reduced pteridine as one donor |
| 2. Transferases | | |
| 2.1 | Transferring one-carbon groups | |
| | 2.1.1 | Methyltransferases |
| | 2.1.2 | Hydroxymethyl-, formyl- and related transferases |
| | 2.1.3 | Carboxyl- and carbamoyltransferases |
| | 2.1.4 | Amidinotransferases |
| 2.2 | Transferring aldehydic or ketonic residues | |
| 2.3 | Acyltransferases | |
| | 2.3.1 | Acyltransferases |
| | 2.3.2 | Aminoacyltransferases |
| 2.4 | Glycosyltransferases | |
| | 2.4.1 | Hexosyltransferases |
| | 2.4.2 | Pentosyltransferases |
| 2.5 | Transferring alkyl or related groups | |
| 2.6 | Transferring nitrogenous groups | |
| | 2.6.1 | Aminotransferases |
| | 2.6.3 | Oximinotransferases |
| 2.7 | Transferring phosphorus-containing groups | |
| | 2.7.1 | Phosphotransferases with an alcohol group as acceptor |
| | 2.7.2 | Phosphotransferases with a carboxyl group as acceptor |
| | 2.7.3 | Phosphotransferases with a nitrogeneous group as acceptor |
| | 2.7.4 | Phosphotransferases with a phospho-group as acceptor |
| | 2.7.5 | Phosphotransferases, apparently intromolecular |
| | 2.7.6 | Pyrophosphotransferases |
| | 2.7.7 | Nucleotidyltransferases |
| | 2.7.8 | Transferases for other substituted phospho-groups |

TABLE II-continued

| | | |
|---|---|---|
| 2.8 | Transferring sulfur-containing groups | |
| | 2.8.1 | Sulfurtransferases |
| | 2.8.2 | Sulfotransferases |
| | 2.8.3 | CoA-transferases |
| 3. Hydrolases | | |
| | 3.1 | Acting on ester bonds |
| | 3.1.1 | Carboxylic ester hydrolases |
| | 3.1.2 | Thiolester hydrolases |
| | 3.1.3 | Phosphoric monoester hydrolases |
| | 3.1.4 | Phosphoric diester hydrolases |
| | 3.1.5 | Triphosphoric monoester hydrolases |
| | 3.1.6 | Sulfuric ester hydrolases |
| | 3.2 | Acting on glycosyl compounds |
| | 3.2.1 | Glycoside hydrolases |
| | 3.2.2 | Hydrolyzing N—glycosyl compounds |
| | 3.2.3 | Hydrolizing S—glycosyl compounds |
| | 3.3 | Acting on ether bonds |
| | 3.3.1 | Thioether hydrolases |
| | 3.4 | Acting on peptide bonds (peptide hydrolases) |
| | 3.4.1 | α-Aminoacyl-peptide hydrolases |
| | 3.4.2 | Peptidyl-aminoacid hydrolases |
| | 3.4.3 | Dipeptide hydrolases |
| | 3.4.4 | Peptidyl-peptide hydrolases |
| | 3.5 | Acting on C—N bonds other than peptide bonds |
| | 3.5.1 | In linear amides |
| | 3.5.2 | In cyclic amides |
| | 3.5.3 | In linear amidines |
| | 3.5.4 | In cyclic amidines |
| | 3.5.5 | In cyanides |
| | 3.5.99 | In other compounds |
| | 3.6 | Acting on acid-anhydride bonds |
| | 3.6.1 | In phosphoryl-containing anhydrides |
| | 3.7 | Acting on C—C bonds |
| | 3.7.1 | In ketonic substances |
| | 3.8 | Acting on halide bonds |
| | 3.8.1 | in C—halide compounds |
| | 3.8.2 | in P—halide compounds |
| | 3.9 | Acting on P—N bonds |
| 4. Lyases | | |
| | 4.1 | Carbon-carbon lyases |
| | 4.1.1 | Carboxy-lyases |
| | 4.1.2 | Aldehyde-lyases |
| | 4.1.3 | Ketoacid-lyases |
| | 4.2 | Carbon-oxygen lyases |
| | 4.2.1 | Hydro-lyases |
| | 4.2.99 | Other carbon-oxygen lyases |
| | 4.3 | Carbon-nitrogen lyases |
| | 4.3.1 | Ammonia-lyases |
| | 4.3.2 | Amidine-lyases |
| | 4.4 | Carbon-sulfur lyases |
| | 4.5 | Carbon-halide lyases |
| | 4.99 | Other lyases |
| 5. Isomerases | | |
| | 5.1 | Racemases and epimerases |
| | 5.1.1 | Acting on amino acids and derivatives |
| | 5.1.2 | Acting on hydroxy acids and derivatives |
| | 5.1.3 | Acting on carbohydrates and derivatives |
| | 5.1.99 | Acting on other compounds |
| | 5.2 | Cis-trans isomerases |
| | 5.3 | Intramolecular oxidoreductases |
| | 5.3.1 | Interconverting aldoses and ketoses |
| | 5.3.2 | Interconverting keto and enol groups |
| | 5.3.3 | Transposing C=C bonds |
| | 5.4 | Intramolecular transferases |
| | 5.4.1 | Transferring acyl groups |
| | 5.4.2 | Transferring phosphoryl groups |
| | 5.4.99 | Transferring other groups |
| | 5.5 | Intramolecular lyases |
| | 5.99 | Other isomerases |
| 6. Ligases or Synthetases | | |
| | 6.1 | Forming C—O bonds |
| | 6.1.1 | Aminoacid-RNA ligases |
| | 6.2 | Forming C—S bonds |
| | 6.2.1 | Acid-thiol ligases |
| | 6.3 | Forming C—N bonds |
| | 6.3.1 | acid-ammonia ligases (amide synthetases) |
| | 6.3.2 | Acid-aminoacid ligases (peptide synthetases) |

TABLE II-continued

| | | |
|---|---|---|
| | 6.3.3 | Cylo-ligases |
| | 6.3.4 | Other C—N ligases |
| | 6.3.5 | C—N ligases with glutamine as N—donor |
| | 6.4 | Forming C—C bonds |

Of particular interest will be enzymes which are in Class 1. Oxidoreductases and Class 3 hyrdolases, although enzymes of Class 2, Transferases, Class 4 Lyases and Class 5, Isomerases, can also be of interest in particular situations.

The following table has specific subclasses of enzymes and specific enzymes within the subclass which are of particular interest. Among the oxidoreductases, those involving NAD or NADP, oxygen or hydrogen peroxide are of particular interest. Among the hydrolases, those involving phosphate and glycosides are of particular interest.

TABLE III

| | | | |
|---|---|---|---|
| 1. Oxidoreductases | | | |
| | 1.1 | Acting on the CH—OH group of donors | |
| | | 1.1.1 | With NAD or NADP as acceptor |
| | | | 1. alcohol dehydrogenase |
| | | | 6. glycerol dehydrogenase |
| | | | 27. lactate dehydrogenase |
| | | | 37. malate dehydrogenase |
| | | | 49. glucose-6-phosphate dehydrogenase |
| | | 1.1.3 | With $O_2$ as acceptor |
| | | | 4. glucose oxidase |
| | | | galactose oxidase |
| | 1.2 | Acting on the aldehyde or keto group of donors | |
| | | 1.2.1 | With NAD or NADP as acceptor |
| | | | 12. glyceraldehyde-3-phosphate dehydrogenase |
| | | 1.2.3 | With $O_2$ as acceptor |
| | | | 2. xanthine oxidase |
| | | | luciferase |
| | 1.4 | Acting on the CH—$NH_2$ group of donors | |
| | | 1.4.3 | With $O_2$ as acceptor |
| | | | 2. L-amino acid oxidase |
| | | | 3. D-amino acid oxidase |
| | 1.6 | Acting on reduced NAD or NADP as donor | |
| | | 1.6.99 | With other acceptors |
| | | | diaphorase |
| | 1.7 | Acting on other nitrogeneous compounds as donors | |
| | | 1.7.3 | With $O_2$ as acceptor |
| | | | 3. Uricase |
| | 1.11 | Acting on $H_2O_2$ as acceptor | |
| | | 1.11.1 | |
| | | | 6. catalase |
| | | | 7. peroxidase |
| 2. Transferases | | | |
| | 2.7 | Transferring phosphorus-containing groups | |
| | | 2.7.1 | Phosphotransferases with CH—OH as acceptor |
| | | | 1. hexokinase |
| | | | 2. glucokinase |
| | | | 15. ribokinase |
| | | | 28. triokinase |
| | | | 40. pyruvate kinase |
| | | 2.7.5 | 1. phosphoglucomutase |
| 3. Hydrolases | | | |
| | 3.1 | Acting on ester bonds | |
| | | 3.1.1 | Carboxylic ester hydrolases |
| | | | 7. cholinesterase |
| | | | 8. psuedo cholinesterase |
| | | 3.1.3 | Phosphoric monoester hydrolases |
| | | | 1. alkaline phosphatase |
| | | | 2. acid phosphatase |
| | | | 9. glucose-6-phosphatase |
| | | | 11. fructose diphosphatase |
| | | 3.1.4 | Phosphoric diester hydrolases |
| | | | 1. phosphodiesterase |
| | | | 3. phospholipase C |
| | 3.2 | Acting on glycosyl compounds | |
| | | 3.2.1 | Glycoside hydrolases |

TABLE III-continued

|     |     |     |
| --- | --- | --- |
|     |     | 1. alpha amylase |
|     |     | 2. beta amylase |
|     |     | 4. cellulase |
|     |     | 17. muramidase |
|     |     | 18. neuraminidase |
|     |     | 21. beta glucosidase |
|     |     | 23. beta galactosidase |
|     |     | 31. beta glucuronidase |
|     |     | 35. hyaluronidase |
|     | 3.2.2 | Hydrolyzing N—glycosyl compounds |
|     |     | 5. DPNase |
| 4. Lyases |     |     |
|     | 4.1 | Carbon-carbon lyases |
|     | 4.1.2 | Aldehyde lyases |
|     |     | 13. aldolyase |
|     | 4.2.1 | Hydro-lyases |
|     |     | 1. carbonic anhydrase |
| 5. Isomerase |     |     |
|     | 5.4 | Intramolecular transferases |
|     | 5.4.2 | Transferring phosphoryl group |
|     |     | triose phosphate isomerase |

Nonenzymatic catalysts may also find use, but will normally not be employed by themselves, but in conjunction with an enzymatic catalyst. Therefore, their use will be discussed in conjunction with the preferential production of the signal generating compound at the solid surface.

Of particular interest in the subject invention is the use of coupled catalysts, usually two or more enzymes, where the product of one enzyme serves as the substrate of the other enzyme. One or more enzymes are bound to the surface, while one enzyme is always bound to a mip. Alternatively, two enzymes can be bound to a mip, with or without an additional enzyme bound to the surface. The solute will be the substrate of any one of the enzymes, but preferably of an enzyme bound to the surface. The enzymatic reaction may involve modifying the solute to a product which is the substrate of another enzyme or production of a compound which does not include a substantial portion of the solute, which serves as an enzyme substrate. The first situation may be illustrated by glucose-6-phosphate being catalytically hydrolyzed by alkaline phosphatase to glucose, wherein glucose is a substrate for glucose oxidase. The second situation may be illustrated by glucose being oxidized by glucose oxidase to provide hydrogen peroxide which would enzymatically react with the signal generator precursor to produce the signal generator.

Coupled catalysts can also involve an enzyme with a non-enzymatic catalyst. The enzyme can produce a reactant which undergoes a reaction catalyzed by the non-enzymatic catalyst or the non-enzymatic catalyst may produce a substrate (includes coenzymes) for the enzyme. For example, Meldola blue could catalyze the conversion of NAD and hydroquinones to NADH which reacts with FMN oxidoreductase and bacterial luciferase in the presence of long chain aldehydes to produce light.

A wide variety of nonenzymatic catalysts which may be employed in this invention are found in U.S. application Ser. No. 815,636, U.S. Pat. No. 4,160,645, the appropriate portions of which are incorporated herein by reference. The nonenzymatic catalysts employ as reactants a first compound which reacts by a 1-electron transfer and a second compound which reacts by a 2-electron transfer, where the two reactants are capable of reacting with each other slowly, if at all, in the absence of the catalyst.

Various combinations of enzymes may be employed to provide a signal generating compound at the surface. Particularly, combinations of hydrolases may be employed to produce an insoluble signal generator. A single exohydrolase may act in a substantially equivalent manner to an enzyme pair by employing the appropriate substrate. Alternatively, combinations of hydrolases and oxidoreductases can provide the signal generator. Also, combinations of oxidoreductases may be used to produce an insoluble signal generator. The following table is illustrative of various combinations which may be employed to provide for preferential production of the signal generating compound at the surface. Usually there will be a preferred catalyst at the surface, since as indicated previously, by appropriate choice of the catalyst at the surface, a greater number of reagents may be combined in a single formulation.

In the following table the first enzyme is intended to be bound to the surface and the second enzyme to a mip, although in particular situations it may be desirable to reverse their positions.

INTERRELATED TWO ENZYME SYSTEMS

| First Enzyme | Second Enzyme | Solute | Signal Generation |
| --- | --- | --- | --- |
| 1. Galactose oxidase | horse radish peroxidase | $\beta$-D-galactose | 4-Cl-1-naphthol dye |
| 2. uricase | horse radish peroxidase | urate | o-dianisidine dye |
| 3. glucose oxidase | microperoxidase | $\beta$-D-glucose | bis-toluidine dye |
| 4. esterase | $\beta$-glucuronidase | 2,2-bis(3'-chloro-4'glucuronyloxyphenyl) phthalide choline chloride ester | 3',3''-dichlorophenolphthalein |
| 5. alkaline phosphatase | peroxidase | 4-Cl-1-naphthyl phosphate | 4-Cl-1-naphthol dye |
| 6. hexokinase | glucose-6-phosphate dehydrogenase | glucose | iodonitrotriphenyl formazan |
| 7. alkaline phosphatase | $\beta$-galactosidase | $O^7$-($\beta$-D-galactosidyl-6'-phosphate) 4-alkylumbelliferone | 4-alkylumbelliferone |

| First Enzyme | Reactions |
| --- | --- |
| 1. Galactose oxidase | 1. galactose + $O_2 \rightarrow$ D-galactono-$\delta$-lactone + $H_2O_2$ |
|  | 2. $H_2O_2$ + 4-Cl-1-naphthol $\rightarrow$ dye |
| 2. uricase | 1. urate + $O_2 \rightarrow$ allantoin + $H_2O_2$ |
|  | 2. $H_2O_2$ + o-dianisidine $\rightarrow$ dye |
| 3. glucose oxidase | 1. glucose + $O_2 \rightarrow$ D-glucono-$\delta$-lactone + $H_2O_2$ |
|  | 2. $H_2O_2$ + bis-toluidine $\rightarrow$ dye |
| 4. esterase | 1. 2,2-bis(3'-chloro-4'-glucuronyloxyphenyl) phthalide choline chloride $\rightarrow$ 2,2-bis (3'-chloro-4'-glucuronyloxyphenyl)-phthalide |
|  | 2. 2,2-bis(3'-chloro-4'-glucuronyloxyphenyl)phthalide $\rightarrow$ 3',3''-dichlorophenolphthalein |
| 5. alkaline phosphatase | 1. 4-Cl-1-naphthyl phosphate $\rightarrow$ 4-Cl-1-naphthol |
|  | 2. 4-Cl-1-naphthol $\rightarrow$ dye |
| 6. hexokinase | 1. glucose + ATP $\rightarrow$ glucose-6-phosphate |
|  | 2. glucose-6-phosphate + NADP $\rightarrow$ NADPH phenazine methosulfate + NADPH + triphenyltetrazolium chloride $\rightarrow$ formazan |
| 7. alkaline phosphatase | 1. $O^7$-($\beta$-D-galactosidyl-6'-phosphate)-4-alkylumbelliferone $\rightarrow$ $O^7$-($\beta$-D-galactosidyl) 4-alkylumbelliferone |

| | 2. $O^7$-($\beta$-D-galactosidyl) 4-alkylumbelliferone → 4-alkylumbelliferone | | | |
|---|---|---|---|---|
| INTERRELATED ENZYME AND NON-ENZYMATIC CATALYST SYSTEMS | | | | |
| | Enzyme on mip | Catalyst | Solute | Signal Generation* |
| 1. | G-6-PDH | Meldola blue | NAD | formazan |
| 2. | lactate dehydrogenase | phenazine methosulfate | NAD | benzyl-viologen dye |
| 3. | 3-hydroxy butyrate dehydrogenase | pryocyanine | NAD | formazan |

*Precursor to signal generator may be covalently bonded to solid surface.

| Enzyme on mip | Reactions |
|---|---|
| 1. G-6-PDH | 1. G-6-P + NAD → glucuronate-6-P + NADH<br>2. NADH + triphenyltetrazolium → NAD + formazan |
| 2. lactate dehydrogenase | 1. lactate + NAD → pyruvate + NADH<br>2. NADH + benzyl viologen → NAD + dye |
| 3. 3-hydroxy butyrate dehydrogenase | 1. 3-hydroxybutyrate + NAD → acetoacetate + NADH<br>2. NADH + triphenyltetrazolium → NAD + formazan |

Quite obviously, many of the dyes indicated above may be substituted with other dyes which have the proper solubility requirements or which can be modified to have the proper solubility requirements for the subject invention. In addition, it should be appreciated, that by having a high localized concentration of the dye, the dye will rapidly bind to the surface. In addition, any incremental amount of dye which diffuses from the bulk solution to the surface will not significantly affect the amount of dye which precipitates on the surface. Depending upon the nature of the dye, either light absorption by the dye or, if fluorescent, light emission may be measured. Instead of dyes, electroactive compounds may be produced and electrical properties at the surface measured.

Instead of a chemical reaction of an enzyme product to produce the signal generating compound, the environment of the enzyme product can be selectively modified, upon binding to the surface, so as to produce the signal generating compound. For example, one could hydrolyze an ester or ether to produce an insoluble colorless form of a pH sensitive dye at the surface. The local pH at the surface will be made substantially different from the bulk solution by having changed groups on the surface. By employing a signal generating compound which is sensitive to proton concentration, the observed signal from the product bound to the surface would differ greatly from the product in the bulk solution or liquid phase. Fluorescer quencher pairs may also be employed where the solute produces an insoluble quencher molecule, which binds to the surface. Increasing amounts of the quencher molecule on the surface will result in substantially decreased fluorescence from the fluorescent molecules bonded to the surface.

Besides acid-base effects and fluorescer and quencher pairs, other interactions may include enzyme inhibitor-enzyme combinations, medium effects caused by hydrophobic binding, redox reactions, covalent coupling to form surface bound dyes, or the like.

One can further enhance the differentiation between the concentration of the signal generator at the solid surface as compared to the signal generator in the solution, by having a scavenger for a member of the signal producing system. The role of the scavenger is to interact with a component of the signal producing system to inhibit the functioning of the component in the production of the detectible signal. The scavenger employed can act in a variety of ways.

The first way is to employ a scavenger for the signal generator which interacts with the signal generator to inhibit its formation of a signal. This inhibition can be as a result of a chemical reaction or specific or nonspecific binding. So far as a chemical reaction, a wide variety of chemical reactions can be employed depending upon the nature of the signal generator. For example, if the dye goes from a leuco to a colored form by virtue of an oxidation-reduction reaction, by providing for reversing the reaction in the bulk solution, the colored form can be substantially minimized in the bulk solution. The chemical scavenger employed should either react with the signal generator on the surface extremely slowly or not at all. Convenient scavengers would be enzymes which would reverse the redox reaction or antibodies which would modify the absorption or emission characteristics of a dye. Enzymes or antibodies could be employed which are monomeric or polymeric e.g. bound to particles, so as to reduce their ability to interact with the signal generator on the surface.

Instead of scavengers for the signal generator, one may employ a scavenger for a different member or intermediate of the signal generating system. One can utilize the steric bulk of the surface to discriminate between catalyst bound to the surface and catalyst in the bulk solution. By employing inhibitory antienzyme bound to particles, enzymes in the bulk solution would be inhibited from reacting when the antienzyme bound to the enzyme, while the enzyme bound to the surface would be free to react. Similarly, one could provide other inhibitors bound to particles with which the enzyme reacts resulting in destruction of the enzyme activity.

Where two enzymes are involved so that an intermediate product is involved, one could employ as the scavenger a reactant which destroys the intermediate. For example, where an intermediate product is hydrogen peroxide, by adding catalase, the hydrogen peroxide would be destroyed in the bulk solution. At the surface, however, there would be more effective competition by the relatively concentrated catalyst bound to the surface with the catalase for the hydrogen peroxide. This competition could be made even more favorable by attaching the catalase to particles that are sterically excluded from the surface. With different systems, different techniques can be employed, using the versatility of the subject system to achieve the desired effect.

Finally, one can provide for a compound bonded to the surface which will interact with a product of the catalyzed reaction. For example, one can produce a compound which will react with the compound on the surface to change the compound from the leuco form to the colored form. Illustrative of such a technique would be to oxidize NADH with a nonenzymatic catalyst and a tetrazolium salt bonded to the surface. The catalyst could be, for example, phenazine methosulfate or Meldola Blue. The NADH would react with the catalyst which would promptly react with the tetrazolium salt on the surface to form the dye. One could conveniently couple this with a scavenger, such as an oxidant which reoxidized the reduced catalyst, so that any reduced catalyst which was formed in the bulk solution would be rapidly destroyed. A significant alternative would be, for example, 1,7-naphthalenediol bound to the surface which captures aminoantipyrene oxidation product produced by HRP. Less chromogenic nucleophiles could act as scavengers.

The next element of the signal producing system is the solute. The solute will be the initial reactant subject to catalytic transformation to a product. As already discussed, the product can play a number of different roles. The product may be the signal generator which becomes bound to the solid surface. Alternatively, the product may be an intermediate which serves as a substrate for a second catalyst, which further transforms the product to provide the signal generator. Alternatively, the solute can undergo a reaction which leads to a compound which then reacts with another compound to produce the signal generator. The other compound may be free in solution or bound to the solid surface, with the reaction being either catalyzed or uncatalyzed.

ANCILLARY MATERIALS

Various ancillary materials will frequently be employed in the subject assays. Particularly, enzyme substrates, cofactors, activators, scavengers, inhibitors or the like may be included in the assay medium.

In addition, buffers will normally be present, as well as stabilizers. Frequently in addition to these additives, additional proteins may be included, such as albumins; or surfactants, particularly non-ionic surfactants, e.g. polyalkylene glycols, or the like.

COMPOSITIONS

Novel compositions and solid test films or strips are provided, as well as combinations of reagents for use in the determination of a wide variety of analytes. Of particular interest are haptens having physiologic activity, covalently bonded to a solid porous support to which is also covalently bonded an enzyme, particularly a redox enzyme or a hydrolase. The solid supports are used in conjunction with a receptor to which is bonded an enzyme, where the enzyme-bound-receptor employs the product of the enzyme-bound-solid support as a substrate. Included with the enzyme-bound-receptor is the substrate for the enzyme-bound-solid support. Impregnated in the solid support may be buffers, substrates and cofactors for the enzyme on the solid support other than the substrate or cofactor combined with the enzyme-bound-receptor. The amounts of the various reagents are optimized to enhance the sensitivity of the assay for the analyte.

For an antigenic analyte, either the receptor for the antigen or the antigen may be covalently bonded to the solid support along with an enzyme. The solid support containing the receptor or antigen and the enzyme is analogous to the solid support with the hapten.

Alternatively, a solid support can be employed having a mono- or polyepitopic antigen or receptor bound to it in conjunction with a covalently bonded electrophilic or nucleophilic coupler. The coupler can react with its appropriate partner. For example, with a nucleophilic coupler bound to the support, oxidized forms of developers, such as aromatic amines may be employed as coupling partners to form dyes. The reduced form of the dye may be used as the solute in conjunction with an enzyme-bound-mip, where the enzyme is an oxidoreductase, such as peroxidase. The peroxidase will oxidize the reduced form of the developer e.g. aromatic amine, which will react with the coupling agent on the support to produce a dye. Illustrative coupling agents include phenols, $\beta$-diketones, pyrazalones, and the like.

Finally, a solid support can be employed having a hapten, antigen or antibody in conjunction with a compound covalently bonded to the solid support which can react with the reduced form of Medola Blue, phenazine methosulfate or methylene blue to go from a leuco form to a colored form. The strips will be used in conjunction with the oxidized form of the aforementioned reductants, an enzyme-antibody conjugate, where the enzyme desirably produces NADH or NADPH or other reductant which will react with the aforementioned catalytic reductants, which in turn will react with the leuco form of the dye on the solid support.

EXPERIMENTAL

The following examples are offered by way of illustration and not by way of limitation.

All percents and parts not otherwise indicated are by weight, except for mixtures of liquids which are by volume. When a solvent is not indicated, water is intended. All temperatures not otherwise indicated are centigrade. The following abbreviations are employed: CMM-$O^3$-carboxymethyl morphine; HRP-horse radish peroxidase; NHS-N-hydroxy succinimide; EDCI-N-ethyl N'-(3-dimethylaminopropyl) carbodiimide; DMF-N,N-dimethyl formamide; THF-tetrahydrofuran; BSA-bovine serum albumin; HIgG-human immunoglobulin G; THC-tetrahydrocannabinol derivative; RT-room temperature; GO-glucose oxidase.

EXAMPLE 1

Morphine-Horseradish Peroxidase (HRP) Conjugate

Into a reaction flask was combined 10 $\mu$moles $O^3$-carboxymethylmorphine, 11 $\mu$moles of N-hydroxy succinimide and 12 $\mu$moles of EDCI in a total volume of about 12.1 ml in DMF. After combining the reagents, the mixture was flushed with nitrogen and stirred overnight in a cold room. To 0.5 ml HRP (2 mg) in 50 mM aqueous sodium carbonate (pH 9.5) was added 150 ml DMF, followed by 300 $\mu$l of the above ester solution and the mixture allowed to stand overnight at 4°. The reaction mixture was then applied to a 2$\times$30 cm column of G50 Sephadex and eluted with 0.05 M tris, pH 7.6, 0.1 M KCl and the protein monitored. The fractions in the void volume were pooled to provide 0.5 ml having a conentration of 0.2 mg/ml. By employing a radioactive tracer, the morphine/HRP molar ratio was found to be 1.86 with a concentration of HRP of 200 $\mu$g/ml.

EXAMPLE 2

Protein Coupling to Paper Filter Disk-Morphine

The following is the exemplary protocol employed for protein coupling to a paper support. Whatman #2 filter paper disks 7 cm dia. were activated in 0.1 M sodium periodate for 5 hrs. at room temperature. After washed with water extensively, and drying in THF, 1 ml of the appropriate protein solution in 0.2 M borate, pH 8.5, 0.5 M NaCl, 0.1 M NaBH$_3$CN was added to the disks and the mixture allowed to stand overnight at 4°. To the mixture was then added 1.4 ml 50 mM Bicine buffer, pH 8.5, containing 2 mg NaBH$_4$ and the mixture allowed to stand for 3 hrs. at room temperature, followed by termination by washing the disks in 1 M borate, pH 8.5, 50 mM Bicine, 0.2 M KCl. The wash was about 20 ml and the protein in the wash was determined, with the amount of protein bound to the disk determined by the difference.

The following table indicates the different protein solutions employed and the concentration of protein on various disks in $\mu g/cm^2$.

TABLE IV

| Protein in 1:5 ml of Solution[1] | Total Protein Coupled to disc $\mu g/cm^2$ |
|---|---|
| 10 mg $Ab_M$ | 24.3 |
| 10 mg $Ab_M$, $5A_{280}GO$ | 45.6 |
| 5 mg $Ab_M$, $5A_{280}GO$ | 6.53 |
| 5 mg $Ab_{HIgG}$, $5A_{280}GO$ | 7.39 |
| 5 mg $Ab_{G(RIg)}$, $5A_{280}GO$ | 8.69 |

[1]$Ab_M$ — antibody to morphine
$5A_{280}GO$ — glucose oxidase at a concentration having an absorption of 5 at $A_{280nm}$ per cm
$Ab_{HIgG}$ — antibody to human γ-globulin G
$Ab_{G(RIg)}$ — antibody to rabbit γ-globulin G from goat antisera In order to demonstrate the subject invention, a number of determinations were carried out to determine the effect of having ligand analyte present in the assay medium.

The following sample solutions were prepared. The disk is indicated by the particular protein(s) bound to the paper.

TABLE V

| # | Paper[1] | HRP-M[2] $\mu l$ | CMM[3] $\mu l$ | RIg-HRP[4] $\mu l$ | RIg[5] $\mu l$ |
|---|---|---|---|---|---|
| 1. | $Ab_M$ | 30 | 0 | — | — |
| 2. | $Ab_M$ | 30 | 0 | — | — |
| 3. | $Ab_M$ | 30 | 30 | — | — |
| 4. | $Ab_M$ | 30 | 30 | — | — |
| 5. | $Ab_M GO(2:1)$ | 30 | 0 | — | — |
| 6. | $Ab_M GO(2:1)$ | 30 | 0 | — | — |
| 7. | $Ab_M GO(2:1)$ | 30 | 30 | — | — |
| 8. | $Ab_M GO(2:1)$ | 30 | 30 | — | — |
| 9. | $Ab_{GAR}GO$ | — | — | 44 | 0 |
| 10. | $Ab_{GAR}GO$ | — | — | 44 | 0 |
| 11. | $Ab_{GAR}GO$ | — | — | 44 | 10 |
| 12. | $Ab_{GAR}GO$ | — | — | 44 | 10 |

[1]Whatman filter paper (∼6mm dia)
$Ab_M$ — morphine antisera (∼6.08 μgAb per disk)
$Ab_M GO(2:1)$ — morphine antisera plus glucose oxidase; 2:1 mole ratio in reaction medium (7.6 μgAb per disc)
$Ab_{GAR}GO$ — goat anti(rabbit IgG) plus glucose oxidase 1:1 mole ratio in reaction medium (∼2.2 μgAb per disk)
[2]HRP-M — morphine conjugated to horse radish peroxidase and product diluted (20 μg/ml)
[3]CMM — $O^3$-carboxymethyl morphine (90 μg/ml)
[4]RIg-HRP — rabbit immunoglobulin G conjugated to horse radish peroxidase (13.8 μgAb/ml)
[5]$RAb_{HIgG}$ — rabbit immunoglobulin G The protocol was as follows. The disk and CMM or RIg were combined employing 0.94 μl of buffer, the buffer being 50 mM tris, pH 7.6, 100 mM KCl, and 0.1 mg/ml BSA. The mixture was incubated for 5 hrs followed by the addition of HRP-M or Rig-HRP in 1 ml of the appropriate reaction buffer to the incubation buffer or the disk was removed from the incubation buffer, washed with 1 ml of water, and then combined with the HRP-M or RIg-HRP in the reaction buffer. Depending upon whether glucose oxidase was present on the paper, the reaction buffers differed in that in the absence of glucose oxidase, 20 μl of 90 mM hydrogen peroxide was added in addition to sufficient o-dianisidine to provide 0.1 mg/ml. In the presence of glucose oxidase, the buffer was made 50 mM in glucose and no hydrogen peroxide was added.

The odd number examples were carried out retaining the disk in the incubation buffer and adding reaction buffer, while the even numbered examples were carried out with the removal of the disk from the incubation buffer, and washing and then combining the disk and reaction buffer.

In each case, 1 ml of the reaction buffer was employed, and in the odd numbered examples, a 60 min incubation was employed. In the Exs. 1, 3, 5, and 7, 20 μl of 3.9 mg/ml catalase (30,000 U/mg) was also included, while in Exs. 9 and 11 only 10 μl of the catalase solution was included. In the even numbered examples, no catalase was added.

In each of Exs. 1, 5, and 9, the disks were darker than the comparable Exs. 3, 7, and 11 respectively, showing that the presence of a ligand did allow for discrimination in result.

In the even numbered assays, the reactions for 2, 4, 6 and 8 were carried out for 5 mins, while for 10 and 12, 10 mins. The results were far more dramatic with the even numbered examples, where the disk was clearly white in the presence of the ligand and a dark brown in the absence of the ligand.

The results clearly demonstrate that one can assay for a ligand, both haptenic and antigenic, or a receptor, by employing a catalyst bound to a mip, which becomes distributed between a surface and the bulk assay medium in proportion to the amount of ligand or receptor present in the medium. In the subject situation, an insoluble signal generator is produced which becomes bound to the surface and allows for measurement of the signal in relation to the amount of analyte in the assay medium.

In the next study, the effect on the amount of signal generator produced in relation to varying concentrations of analyte was evaluated. In effect, a standard curve was prepared, relating the signal generator produced on the surface to the amount of analyte in the medium. The protocol was as follows.

To tubes containing 500 μl buffer (50 mM tris, pH 7.6, 200 mM KCl, 2 mg/ml BSA), was added 20 μl of the HRP-morphine conjugate (0.2 μg) followed by 20 μl of a $O^3$-carboxymethylmorphine solution at varying concentrations. To the tube was then added a 6 mm disk of $Ab_M GO$ (2:1) and the mixture incubated at 3 hrs at room temperature.

The disk was then developed in three different ways. In the first way, the supernatant was removed from the disk, 1 ml buffer added and removed. Then, 1 ml of the development buffer (100 mM phosphate, pH 6.0, 200 mM KCl, 0.1 mg/ml o-dianisidine) and 10 μl 90 mM hydrogen peroxide were added and the mixture allowed to react for 5 mins, followed by washing; in the second method, the same procedure was employed, except that 2 ml of buffer was added which did not contain the hydrogen peroxide, but was 15 mM in β-D glucose. The reaction was allowed to proceed for 30 mins., followed by removing the disk, washing and drying. In the third technique, the second technique was repeated, except that 10 μl of a 3.9 mg/ml catalase solution was added.

In each case, there was a steady progression of increased darkness of the solid surface in going from the stock solution of 90 μg/ml of $O^3$-carboxymethylmorphine through 1:5 serial dilutions to a final amount of $1.6 \times 10^{-12}$ mole. The midpoint was found to be $1.2 \times 10^{-10}$ mole or about 40 ng of $O^3$-carboxymethylmorphine.

A second series of studies were performed using morphine as an exemplary ligand. This study involved different sample fluids which would provide varying backgrounds when performing the assay. The reagents were prepared as follows.

EXAMPLE 3

Protein Coupling to Paper Filter Disk-Morphine

In 0.1 M NaIO$_4$ was incubated 12.5 cm of Whatman #2 paper for 5 hrs at RT. The paper was then incubated in 1 M ethylene glycol for 20 min followed by washing with 6 l of deionized water. To the paper was then added a total of 1.8 ml of the appropriate protein solutions in 50 mM borate, 0.2 M NaCl, pH 8.6 and the paper contacted with the protein solution for 2 hrs at RT. The following gives the compositions of the protein solutions.

| | PROTEIN SOLUTIONS | | |
|---|---|---|---|
| | Ab$_M$ | G.O.[1] mg protein | BSA |
| (1) | 4 | 1 | |
| (2) | 1 | 1 | 3 |
| (3) | 0.25 | 1 | 3.75 |
| (4) | 1 | 4 | |
| (5) | 1 | 0.25 | 3.75 |

[1] Absorbance per cm at 280 nm

To the paper was then added 2 ml 2 mg/ml NaBH$_4$ in the same buffer and the mixture allowed to stand for 1 hr at RT. The paper was then washed with water and buffer, then immersed in a solution of 5 mg/ml BSA, 15% sucrose and removed and lyophilized.

For use in assays, ⅜" disks were punched and the disks incubated in urine for 7 min at RT, where the urine had either no morphine or 100 ng/ml morphine. The disks were then transferred to 1 ml of developer solution: 0.1 mg/ml 4-Cl-1-naphthol, 2 mg/ml BSA, 50 mM glucose, 0.1 M PO$_4$, pH 7.0, 0.2 M NaCl and 0.1 mg/ml o-dianisidine. To the solution was then added 4 μl HRP-M (20 μg/ml) and the mixture followed to stand for 30 min at RT and the tests repeated with 15 μl HRP-M and a reaction time of 60 min.

In both cases the presence of the morphine was clearly detectable for (1) and (4), with less difference with the other samples. Thus, the assay is able to detect minute amounts of morphine in the complex proteinaceous urine mixture.

The next study was to determine whether morphine could be detected in milk. The above procedure was repeated employing 1 ml raw whole milk with and without 100 ng/ml morphine. The procedure was varied by employing 100 μl of 2 μg/ml HRP-M and 10 μl of 3.9 mg/ml catalase and incubating for 60 min at RT with a developer solution of the following composition: 50 mM bicine, pH 8.0, 200 mM KCl, 2 mg/ml BSA, 50 mM β-D-glucose and 0.1 mg/ml 4-Cl-1-naphthol. The difference between the samples with and without morphine was clearly detectable using disks prepared employing 1:1 of the Ab$_M$:GO solutions (see Table IV).

In the next study, the use of a solid surface conjugated with a mip was employed for the determination of HigG. In 0.5 ml buffer containing 20 μl of an appropriate HIgG concentration were incubated 6 mm paper disks (Ab$_{HIgG}$GO) for 3 hrs at room temperature. The supernatant was removed, the disks washed, and 0.5 ml buffer added plus 50 μl of a 13.8 μg/ml solution of Ab$_{HIg}$-HRP (DAKO). The mixture was then incubated for 3 hrs at room temperature followed by the addition of 1 ml of 100 mM phosphate, 200 mM KCl, 50 mM glucose and 0.1 mg/ml o-dianisidine. After 30 mins at room temperature, the disks were removed and washed, demonstrating a clear progression in the color of the disks in going from 0.16 and 20 μg of HIgG.

EXAMPLE 4

THC-HRP Conjugate

Into a reaction flask was introduced 0.19 ml of a 0.04 M solution of the NHS ester of 0-carboxymethyl oxime of 7,9,12-hexahydro-6,6-dimethyl-9-oxo-3-pentyldibenzo[b,d]pyran-1-ol in DMF, 0.28 ml HRP (1.5 mg), 0.1 ml 1 M Na$_2$CO$_3$, pH 9.5, and 0.3 ml H$_2$O and the mixture stirred overnight. After centrifuging to remove insoluble material, the supernatant was dialyzed against 0.1 M NaHCO$_3$, 0.5 M NaCl (4 l). The residue was chromatographed on a 20×1.5 cm Sephadex G50 column in 50 mM tris, pH 7.6, 0.2 ml and the void volume peak isolated, ~3 ml, 0.26 mg/ml.

EXAMPLE 5

Protein Coupling to Paper Filter Disk-THC

The following protein solutions in 50 mM borate, pH 8.5, 0.2 M KCl were employed: antitetrahydrocannabinol, IgG, 23 mg/ml; glucose oxidase, 18A$_{280}$/ml.

Paper disks (Whatman #1, 9 cm) were activated in 0.1 M NaIO$_4$ for 4 hr at RT followed by washing with ~3 l H$_2$O. To an activated disk was added 2.5 ml of a protein solution containing 3.83 A$_{280}$/cm glucose oxidase and 0.75 mg of antisera for tetrahydrocannabinol and the mixture allowed to react for 1 hr at RT followed by the addition of 0.5 ml of a 4 mg/ml NaBH$_4$ solution and the reaction mixture allowed to stand for 1.5 hr at RT, turning the disk every 20 min. The disk was then washed with 300 ml 0.5 MNaCl, H$_2$O (2x) and stored moist at 4°.

In order to demonstrate the subject method for THC, disks (~6 mm) were employed with 1 ml urine spiked with varying concentrations of THC. The urine sample was contacted with the disk for 10 min at RT and the disk then transferred to a developer solution containing 10 μl of a 1/100 dilution of the above THC-HRP in 1 ml 50 mM glucose, 50 mM barbitol acetate buffer, pH 7.6, 0.1 mg/ml 4-Cl-1-naphthol and reaction allowed to proceed at RT for 1 hr. At the end of that term the disk in the urine containing 4.7 ng/ml THC could be clearly distinguished from the negative urine sample.

In accordance with the subject invention, a simple sensitive technique is provided for determining analytes at extremely low concentrations and providing for a relatively permanent record of the result. The subject technique allows for assays which can be carried out without highly trained personnel. Depending upon the rate at which the members of the immunological pair bind, various incubation times may be required, while development of the signal can be performed over relatively short times. Furthermore, the samples can be used neat or with only minor dilution, so as to enhance the rate of binding of the members of the immunological pair to the solid surface.

The subject method provides for qualitative and quantitative determination of haptens, antigens and receptors, where standards can be performed to relate signal to concentration. Visual observation of the solid surface may be sufficient for qualitative or semiquantitative determinations, while instrumentation can be employed to enhance the quantitative nature of the result. A substantial variety of techniques may be employed to insure differentiation between the signal generator produced at the surface and any signal generator produced in the bulk solution. Thus, the signal generated at the surface can be directly related to the amount of analyte in the medium.

The subject method differs from prior art methods in providing a method for determining extremely low concentrations of analytes by a simple protocol with a minimum number of steps and reagent formulations. Furthermore, the subject method involves a competition for binding sites or a cooperation between binding sites of mips to have a catalyst bind to a surface to provide a signal generating compound associated with the surface. This is achieved without requiring separation between the catalyst bound to the surface and the catalyst in solution.

Since the use of the surface as a "dip stick" for measuring analytes can be directed to use by non-technical people—even for use in the home—it is important that the method have as few individual steps as possible, be relatively foolproof, particularly by allowing for a control which can be carried out under substantially identical conditions, and have as few measurements as possible. The subject invention fulfills these goals to a substantial degree.

Although the foregoing invention has been described in some detail by way of illustration and example for purposes of clarity of understanding, it will be obvious that certain changes and modifications may be practiced within the scope of the appended claims.

We claim:

1. A kit for use in an immunoassay comprising in combination:
    (a) an insoluble porous surface to which is bound (1) a member of an immunological pair consisting of ligand and immunoglobulin antiligand and (2) an enzyme;
    (b) an enzyme bound to a member of an immunological pair consisting of ligand and an immunoglobulin antiligand; and
    (c) a leuco dye which undergoes an enzymatically catalyzed reaction to produce an insoluble dye,
    wherein the amount of enzyme bound to said member of an immunological pair is related to the amount of said member of an immunological pair bound to an insoluble surface in a ratio to substantially optimize the sensitivity of said immunoassay, wherein said enzyme bound to said porous surface and said enzyme bound to said member of an immunological pair are related by the product of one being the substrate of the other.

2. A kit according to claim 1, wherein said enzymes are oxidoreductases.

3. A kit according to claim 1, wherein said enzyme bound to said member of an immunological pair is horseradish peroxidase.

4. A kit according to any of claims 1, 2 or 3, wherein said enzyme bound to said insoluble porous surface is glucose oxidase.

5. A kit according to claim 4, wherein said leuco dye is a naphthol.

6. A method for detecting the presence of an antiligand analyte in a sample suspected of containing said analyte, wherein said antiligand analyte is a member of an immunological pair (mip) consisting of ligand and homologous antiligand;
    said method involving (1) the partitioning in relation to the amount of analyte in said sample of a first enzyme bound to a mip—enzyme-bound-mip—between a surface of a liquid phase, said surface being porous and permitting approach and binding of enzyme-bound-mip to mip bound to said surface—mip-bound-surface—either directly or in combination with said ligand, where said partitioning is through the intermediacy of ligand-antiligand binding to a mip-bound-surface to which a second enzyme is bound, where said second enzyme is related to said first enzyme by the product of one being the substrate of the other and where said first and second enzymes are oxido reductases; and (2) the change in concentration of a signal generating compound associated with said surface, said change in concentration being in relation to the amount of reaction product produced by said enzyme bound to said surface;
    said method comprising:
    (a) combining in an aqueous assay medium,
        (1) said sample;
        (2) mip-bound-surface, wherein substantially all of said surface and said mip-bound-surface is uniformly contacted with said sample;
        (3) enzyme-bound-mip; and
        (4) the remaining members of the signal producing system, which includes a solute system which is capable of undergoing a catalyzed reaction to produce a product which results in a change in amount of a signal generating compound associated with said surface and capable of producing a detectible signal;
    (b) waiting a sufficient time for enzyme-bound-mip to diffuse to said surface and at least a portion of said enzyme-bound-mip to bind to said surface through the intermediacy of ligand-antiligand binding to result in a change in the amount of signal generating compound associated with said surface in relation to the amount of analyte in said sample; and
    (c) determining the intensity of said detectible signal at said surface as a function of the amount of analyte in said sample.

7. A method according to claim 6, wherein said first enzyme is horseradish peroxidase and said second enzyme is glucose oxidase.

8. A method according to claim 7, wherein said signal generating compound is a leuco dye.

9. A method according to claim 8, wherein said leuco dye is a 1-naphthol.

* * * * *